US009271455B2

(12) United States Patent
Wu et al.

(10) Patent No.: US 9,271,455 B2
(45) Date of Patent: Mar. 1, 2016

(54) SOYBEAN POLYMORPHISMS AND METHODS OF GENOTYPING

(75) Inventors: Kunsheng Wu, Ballwin, MO (US); John LeDeaux, Creve Coeur, MO (US); David Butruille, Des Moines, IA (US); Anju Gupta, Ankeny, IA (US); Richard Johnson, Urban, IL (US); Sam Eathington, Ames, IA (US); Jason Bull, Wildwood, MO (US); Marlin Edwards, Davis, CA (US); Paul McLaird, Lenexa, KS (US)

(73) Assignee: Monsanto Technology LLC, St. Louis, MO (US)

( * ) Notice: Subject to any disclaimer, the term of this patent is extended or adjusted under 35 U.S.C. 154(b) by 1276 days.

(21) Appl. No.: 12/601,461

(22) PCT Filed: May 29, 2008

(86) PCT No.: PCT/US2008/006765
§ 371 (c)(1),
(2), (4) Date: May 25, 2010

(87) PCT Pub. No.: WO2008/153804
PCT Pub. Date: Dec. 18, 2008

(65) Prior Publication Data
US 2010/0275286 A1   Oct. 28, 2010

Related U.S. Application Data

(60) Provisional application No. 60/932,533, filed on May 31, 2007.

(51) Int. Cl.
*A01H 1/04* (2006.01)
*A01H 1/02* (2006.01)
(52) U.S. Cl.
CPC ... *A01H 1/04* (2013.01); *A01H 1/02* (2013.01)
(58) Field of Classification Search
USPC .................................................. 800/267, 312
See application file for complete search history.

(56) References Cited

U.S. PATENT DOCUMENTS

| | | | |
|---|---|---|---|
| 5,210,015 A | 5/1993 | Gelfand et al. |
| 5,217,863 A | 6/1993 | Cotton et al. |
| 5,385,835 A | 1/1995 | Helentjaris et al. |
| 5,437,697 A | 8/1995 | Sebastian et al. |
| 5,468,613 A | 11/1995 | Erlich et al. |
| 5,492,547 A | 2/1996 | Johnson |
| 5,538,848 A | 7/1996 | Livak et al. |
| 5,595,890 A | 1/1997 | Newton et al. |
| 5,616,464 A | 4/1997 | Albagli et al. |
| 5,736,330 A | 4/1998 | Fulton |
| 5,746,023 A | 5/1998 | Hanafey et al. |
| 5,762,876 A | 6/1998 | Lincoln et al. |
| 5,858,659 A | 1/1999 | Sapolsky et al. |
| 5,876,930 A | 3/1999 | Livak et al. |
| 5,945,283 A | 8/1999 | Kwok et al. |
| 5,962,764 A | 10/1999 | Briggs et al. |
| 5,981,832 A | 11/1999 | Johnson |
| 6,004,744 A | 12/1999 | Goelet et al. |
| 6,013,431 A | 1/2000 | Soderlund et al. |
| 6,017,704 A | 1/2000 | Herman et al. |
| 6,030,787 A | 2/2000 | Livak et al. |
| 6,090,558 A | 7/2000 | Butler et al. |
| 6,100,030 A | 8/2000 | McCasky Feazel et al. |
| 6,294,336 B1 | 9/2001 | Boyce-Jacino et al. |
| 6,592,822 B1 | 7/2003 | Chandler |
| 6,599,331 B2 | 7/2003 | Chandler et al. |
| 6,649,414 B1 | 11/2003 | Chandler et al. |
| 6,691,109 B2 | 2/2004 | Bjornson et al. |
| 6,799,122 B2 | 9/2004 | Benson |
| 6,913,879 B1 | 7/2005 | Schena |
| 6,996,476 B2 | 2/2006 | Najarian |
| 2006/0141495 A1 | 6/2006 | Wu |
| 2006/0282911 A1 | 12/2006 | Bull et al. |
| 2006/0288444 A1 | 12/2006 | McCarroll et al. |

FOREIGN PATENT DOCUMENTS

| | | |
|---|---|---|
| EP | 1343911 | 5/2007 |
| WO | 2006122215 | 11/2006 |
| WO | 2008021413 | 2/2008 |

OTHER PUBLICATIONS

Smalley et al (Crop Science 44: 436-442, 2004).*
Meksem et al (Molecular Breeding 7: 63-71, 2001).*
Hall et al., "Using Association Mapping to Dissect the Genetic Basis of Complex Traits in Plants", Briefings in Function Genomics, 2010, pp. 157-165, vol. 9 No. 2.
Fernandez et al., "The Use of ISSR and RAPD Markers for Detecting DNA Polymorphism, Genotype Identification and Genetic Diversity Among Barley Cultivars with Known Origin", Theoretical and Applied Genetics, Apr. 2002, pp. 841-851, vol. 104 Issue 5.
Bi et al., "Single Nucleotide Polymorphisms and Insertion-Deletions for Genetic Markers and Anchoring the Maize Fingerprint Contig Physical Map", Crop Science, 2006, pp. 12-21, vol. 46.
Borevitz et al., "Large-Scale Identification of Single-Feature Polymorphisms in Complex Genomes", Genome Research, 2003, pp. 513-523, vol. 13.

(Continued)

*Primary Examiner* — Keith Robinson
(74) *Attorney, Agent, or Firm* — Thompson Coburn LLP; William A. Holtz

(57) ABSTRACT

Polymorphic soybean DNA loci useful for genotyping between at least two varieties of soybean. Sequences of the loci are useful for providing the basis for designing primers and probe oligonucleotides for detecting polymorphisms in soybean DNA. Polymorphisms are useful for genotyping applications in soybean. The polymorphic markers are useful to establish marker/trait associations, e.g. in linkage disequilibrium mapping and association studies, positional cloning and transgenic applications, marker-aided breeding and marker-assisted selection, hybrid prediction and identity by descent studies. The polymorphic markers are also useful in mapping libraries of DNA clones, e.g. for soybean QTLs and genes linked to polymorphisms.

6 Claims, 3 Drawing Sheets

(56) References Cited

OTHER PUBLICATIONS

Fan et al., "High-Resolution Association Mapping of Quantitative Trait Loci: A Population-Based Approach", Genetics, pp. 663-686, vol. 172, 2006.

Jansen et al., "Genotype-by-environment interaction in genetic mapping of multiple quantitative trait loci": Theoretical and Applied Genetics, 1995, pp. 33-37, vol. 91.

Jansen, Ritsert C., "Mapping of quantitative trait loci by using genetic markers: an overview of biometrical models used", Proceedings of the Ninth Meeting of the EUCARPIA Section Biometrics in Plant Breeding, Biometrics in Plant Breeding: Applications of Molecular Markers, 1994, pp. 116-124, The Netherlands.

Kruglyak et al., "A Nonparametric Approach for Mapping Quantitative Trait Loci", Genetics, 1995, pp. 1421-1428, vol. 139.

Wilson et al., "The Sequence of *Zea mays* bac clone CH201-108E11", Genbank Accession No. AC201832, Apr. 4, 2007.

Winlker et al., "On the Determination of Recombinant Rates in Intermated Recombinant Inbred Populations", Genetics, 2003, pp. 741-745, vol. 164.

Lyamichev et al., "Polymorphisms identification and quantitative detection of genomic DNA by invasive cleavage of oligonucleotide probes", Nature Biotechnology, 1999, pp. 292-296, vol. 17.

Mein et al., "Evaluation of Single Nucleotide Polymorphism Typing with Invader on PCR Amplicons and Its Automation", Genome Research, 2000, pp. 330-343, vol. 10.

Zeng, Zhao-Bang, "Precision Mapping of Quantitative Trait Loci", Genetics, 1994, pp. 1457-1468, vol. 136.

Olivier et al., "High-throughput genotyping of single nucleotide polymorphisms using new biplex invader technology", Nucleic Acids Research, 2002, vol. 30 No. 12 e53.

Utz et al., "Comparison of different approaches to interval mapping of quantitative trait loci", Proceedings of the Ninth Meeting of the EUCARPIA Section Biometrics in Plant Breeding, Biometrics in Plant Breeding: Applications of Molecular Markers, 1994, pp. 195-204, The Netherlands.

Arus et al., "Marker-Assisted Selection", Plant Breeding: Principles and Prospects, 1993, pp. 314-331, Chapman & Hall, London.

Lyamichev et al., "Invader Assay for SNP Genotyping", Methods in Molecular Biology: Single Nucleotide Polymorphisms Methods and Protocols, 2002, pp. 229-240, vol. 212, Humana Press.

Boerma et al., "Pollen Movement Within and Between Rows to Male-sterile Soybeans", Crop Science, 1975, pp. 858-861, vol. 15.

Cui et al., "Detecting single-feature polymorphisms using oligonucleotide arrays and robustified projection pursuit", Bioinformatics, 2005, pp. 3852-3858, vol. 21 No. 20.

Jansen et al., "Constructing dense genetic linkage maps", Theoretical and Applied Genetics, 2001, pp. 1113-1122, vol. 102.

Jansen et al., "High Resolution of Quantitative Traits Into Multiple Loci via Interval Mapping" Genetics, 1994, pp. 1447-1455, vol. 136.

Lander et al., "Mapping Mendelian Factors Underlying Quantitative Traits Using RFLP Linkage Maps", Genetics, 1989, pp. 185-199. Vol 121.

Stam, Piet, "Construction of integrated genetic linkage maps by means of a new computer package: JointMap", The Plant Journal, 1993, pp. 739-744, vol. 3 No. 5.

\* cited by examiner

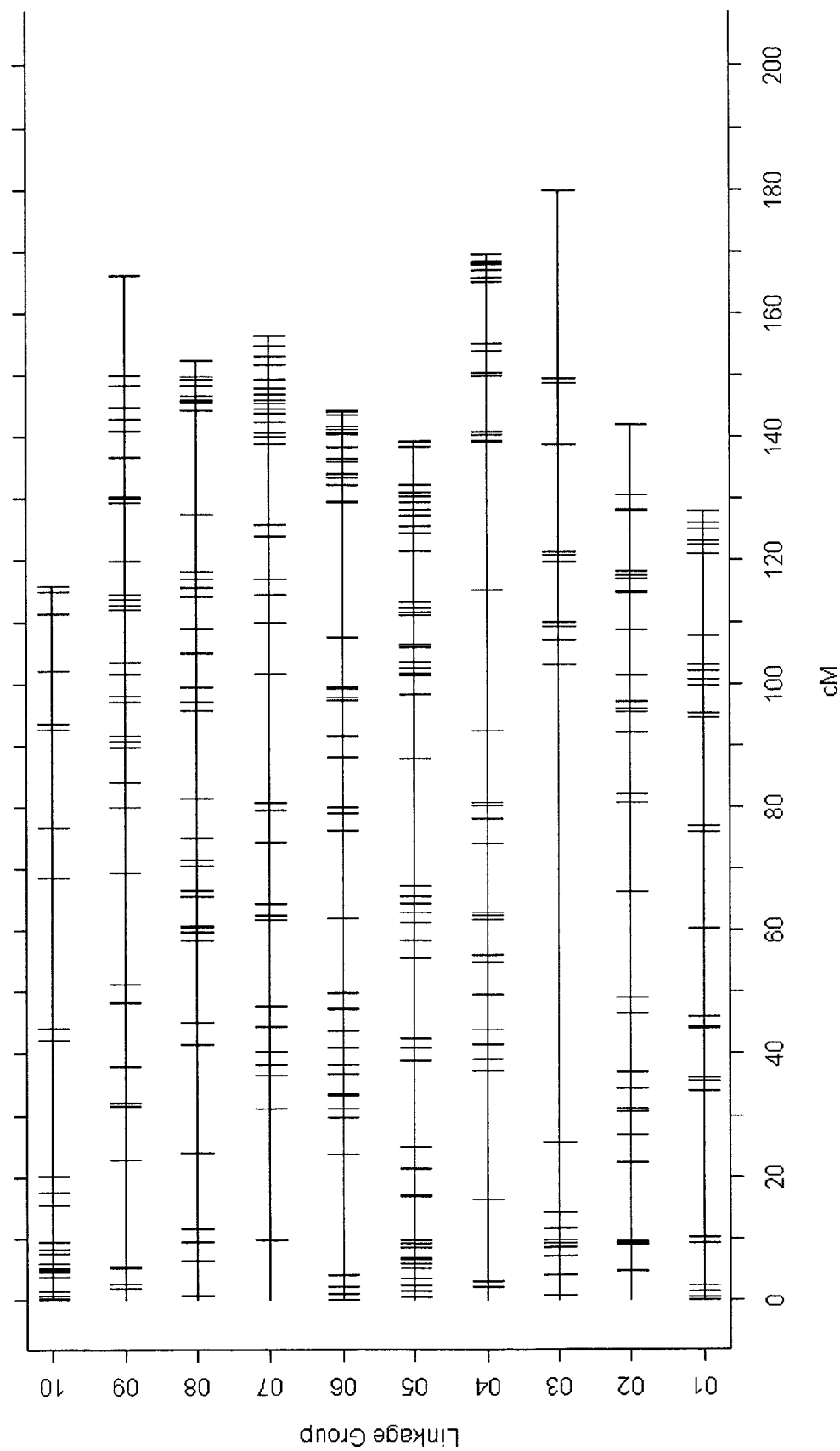

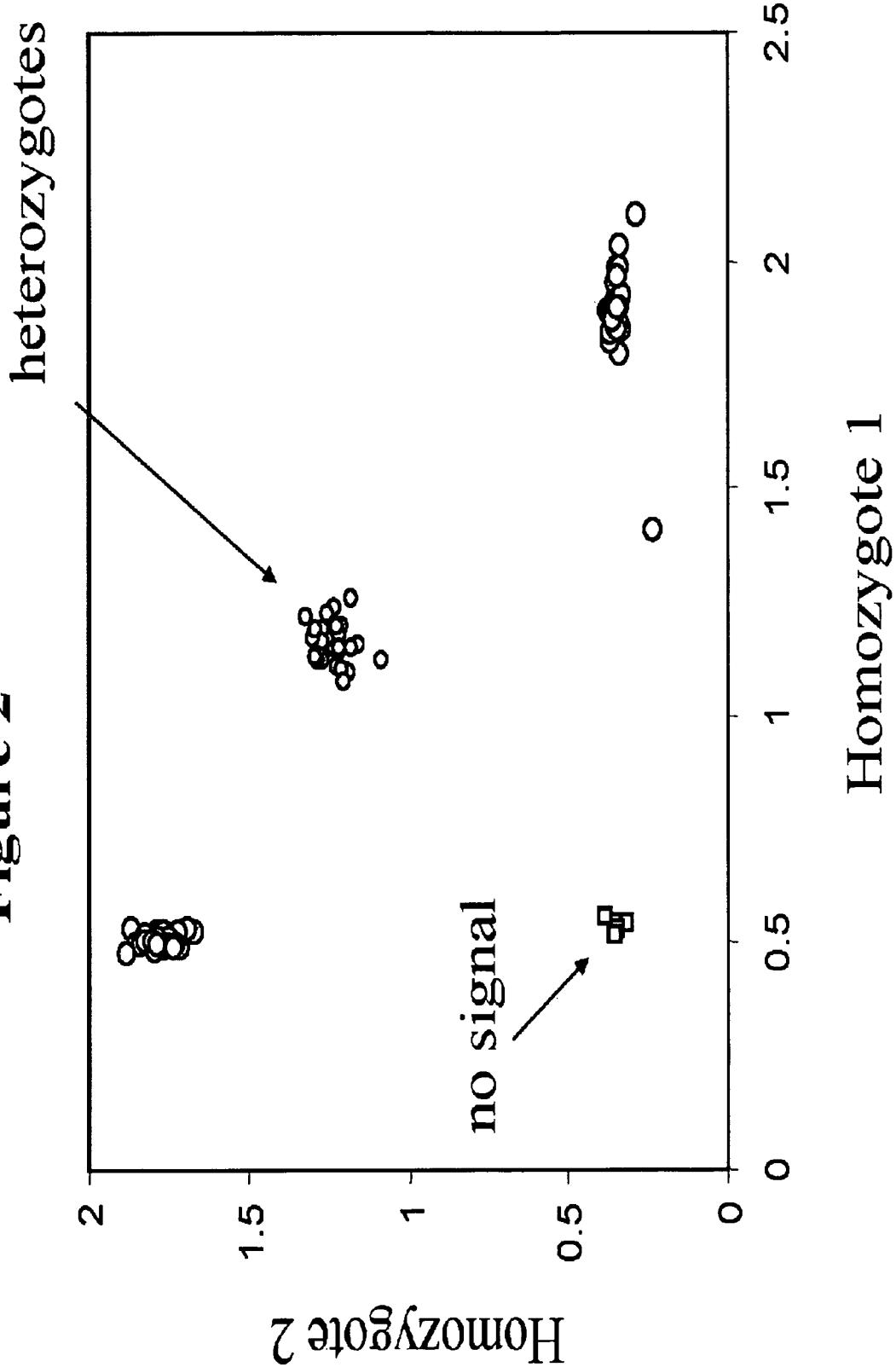

SOYBEAN POLYMORPHISMS AND METHODS OF GENOTYPING

CROSS-REFERENCE TO RELATED APPLICATIONS

This application is a National Stage application of International Patent Application No. PCT/US2008/006765, filed May 29, 2008 and incorporated by reference herein in its entirety, which claims the benefit of U.S. Patent Application No. 60/932,533, filed May 31, 2007 and incorporated by reference herein in its entirety.

STATEMENT REGARDING FEDERALLY SPONSORED RESEARCH OR DEVELOPMENT

Not Applicable.

INCORPORATION OF SEQUENCE LISTING AND TABLES

The sequence listing and a computer readable form (CRF) of the sequence listing are provided herein on CD-ROMs, each containing the file named "46-21(54825).SEQLIST-.txt", which is 7639719 bytes (measured in MS-Windows), all of which were created on May 29, 2007, are herein incorporated by reference. Two copies of Table 1 and Table 3 are also provided herein on CD-ROMs, containing the files named "Table 1" (Copy 1 and Copy 2), which is 14403168 bytes (measured in MS-Windows) and "Table 3" (Copy 1 and Copy 2), which is 82686 bytes (measured in MS-Windows), all of which were created on May 29, 2007, are herein incorporated by reference.

plants that contain a desired genotype at multiple loci, and that are expected to transfer the desired genotype, along with a desired phenotype to their progeny. Molecular marker alleles can be used to identify plants that contain the desired genotype at one marker locus, several loci, or a haplotype, and that would be expected to transfer the desired genotype, along with a desired phenotype to their progeny.

The highly conserved nature of DNA, combined with the rare occurrences of stable polymorphisms, provide molecular markers which can be both predictable and discerning of different genotypes. Among the classes of existing molecular markers are a variety of polymorphisms indicating genetic variation including restriction-fragment-length polymorphisms (RFLPs), amplified fragment-length polymorphisms (AFLPs), simple sequence repeats (SSRs), single feature polymorphisms (SFPs), single nucleotide polymorphisms (SNPs) and insertion/deletion polymorphisms (Indels).

Molecular markers vary in their stability and genomic abundance. SNPs are particularly useful as molecular markers because they are more stable than other polymorphisms and are abundant in plant genomes (Bi et al. Crop Sci. 46:12-21 (2006), Kornberg, DNA Replication, W.H. Freeman & Co., San Francisco (1980)). Because the number of molecular markers for a plant species is limited, the discovery of additional molecular markers is critical for genotyping applications including marker-trait association studies, gene mapping, gene discovery, marker-assisted selection and marker-assisted breeding. The discovery and identification of polymorphisms for use as molecular markers requires a substantial sequencing and bioinformatics effort, requiring large scale sequencing from two or more evolutionarily diverged lines or populations.

LENGTHY TABLES

The patent contains a lengthy table section. A copy of the table is available in electronic form from the USPTO web site (http://seqdata.uspto.gov/?pageRequest=docDetail&DocID=US09271455B2). An electronic copy of the table will also be available from the USPTO upon request and payment of the fee set forth in 37 CFR 1.19(b)(3).

BACKGROUND OF THE INVENTION

1. Field of the Invention

Disclosed herein are soybean polymorphisms, nucleic acid molecules related to such polymorphisms and methods of using such polymorphisms and molecules as molecular markers, e.g. in genotyping.

2. Related Art

Polymorphisms are useful as molecular markers, also termed genetic markers, for genotyping-related applications in the agriculture field, e.g. in plant genetic studies and commercial breeding. Such uses of polymorphisms are described in U.S. Pat. Nos. 5,385,835; 5,437,697; 5,385,835; 5,492,547; 5,746,023; 5,962,764; 5,981,832 and 6,100,030.

In particular, the use of molecular markers in breeding programs has accelerated the genetic accumulation of valuable traits into a germplasm compared to that achieved based on phenotypic data only. Herein, "germplasm" includes breeding germplasm, breeding populations, collection of elite inbred lines, populations of random mating individuals, and biparental crosses. Molecular marker alleles (an "allele" is an alternative sequence at a locus) are used to identify Evolving technologies make certain molecular markers more amenable for rapid, large scale use. In particular, technologies such as high-throughput screening for SNP detection indicate that SNPs may be preferred molecular markers.

SUMMARY OF THE INVENTION

It is in view of the above problems that the present invention was developed. This invention provides a series of molecular markers for soybean. These molecular markers comprise soybean DNA loci which have been discovered by direct sequence analysis of soybean genomic DNA. These molecular markers are useful for a variety of genotyping applications. A polymorphic soybean locus of this invention comprises at least 12 consecutive nucleotides which include or are adjacent to a polymorphism which is identified herein, e.g. in Table 1 or Table 3. As indicated in Table 1 the nucleic acid sequences of SEQ ID NO: 1 through SEQ ID NO: 7800 comprise one or more polymorphisms, e.g. single nucleotide polymorphisms (SNPs) and insertion/deletion polymorphisms (Indels). As indicated in Table 3, certain polymorphisms identified herein have also been mapped to certain soybean chromosomes.

The invention first provides for libraries of nucleic acid molecules that comprise at least two distinct sets of nucleic acid molecules wherein each of said distinct sets of nucleic acid molecules permits typing of a corresponding soybean genomic DNA polymorphism identified in Table 1 or Table 3. In certain embodiments of this aspect of the invention, the library comprises two or more distinct sets of nucleic acid molecules are arrayed on at least one solid support or on at least one microtiter plate. The distinct sets of nucleic acid molecules can be located in a separate and distinct well of a microtiter plate. The distinct sets of nucleic acids can also be located at a distinct interrogation position on the solid support.

Libraries where the nucleic acid molecules are combined in a single mixture are also contemplated. In still other embodiments of the invention, the libraries can comprise at least 8, at least 24, at least 96, or at least 384 distinct sets of nucleic acid molecules wherein each of the sets of nucleic acid molecules permit typing of a corresponding distinct soybean genomic DNA polymorphism identified in Table 1 or Table 3. Libraries comprised of sets of nucleic acid molecules that permit typing of soybean genomic DNA polymorphisms identified in Table 3 that are selected from the group consisting of SEQ ID NO: 3122, 2914, 3984, 3608, 1448, 69, 1261, 3436, 1142, 80, 88, 980, 538, 1925, 3669, 2270, 1397, 3747, 888, 365, 2132, 1972, 459, 762, and 1094 are also contemplated.

The distinct sets of nucleic acid molecules in the libraries can comprise a nucleic acid molecule of at least 12 consecutive nucleotides that include or are immediately adjacent to a corresponding polymorphism identified in Table 1 and wherein the sequence of at least 12 consecutive nucleotides is at least 90% identical to the sequence of the same number of nucleotides in either strand of a segment of soybean DNA which includes or is immediately adjacent to said polymorphism. In other embodiments, the nucleic acid molecule is of at least 15 consecutive nucleotides or of at least 18 consecutive nucleotides. The nucleic acid molecules can further comprise a detectable label or provide for incorporation of a detectable label. This detectable label can be selected from the group consisting of an isotope, a fluorophore, an oxidant, a reductant, a nucleotide and a hapten. Detectable labels can be added to the nucleic acid by a chemical reaction or incorporated by an enzymatic reaction.

The distinct sets of nucleic acid molecules can also comprise: (a) a pair of oligonucleotide primers wherein each of said oligonucleotide primers comprises at least 15 nucleotide bases and permit PCR amplification of a segment of DNA containing one of said corresponding polymorphisms identified in Table 1 or Table 3, and (b). at least one detector nucleic acid molecule that permits detection of a polymorphism in said amplified segment in (a). In such distinct sets of nucleic acids, the detector nucleic acid comprises at least 12 nucleotide bases or comprises at least 12 nucleotide bases and a detectable label, and wherein the sequence of said detector nucleic acid molecule is at least 95 percent identical to a sequence of the same number of consecutive nucleotides in either strand of a segment of soybean DNA in a locus of claim 1 comprising said polymorphism.

The invention also provides computer readable media having recorded thereon at least two soybean genomic DNA polymorphisms identified in Table 1 or Table 3. In other embodiments, at least 8 of the soybean genomic DNA polymorphisms identified in Table 1 or Table 3 are recorded on the computer readable media. Computer readable medium having recorded thereon at least two soybean genomic DNA polymorphisms identified in Table 3 and a corresponding genetic map position for each of said soybean genomic DNA polymorphisms are also provided. In other embodiments, at least 8 of the soybean genomic DNA polymorphisms and corresponding genetic map positions are recorded on the computer readable media.

The invention also provides a computer based system for reading, sorting or analyzing soybean genotypic data that comprises the following elements: (a) a data storage device comprising a computer readable medium wherein at least two soybean genomic DNA polymorphisms identified in Table 1 or Table 3 are recorded thereon; b) a search device for comparing a soybean genomic DNA sequence from at least one test soybean plant to said polymorphism sequences of the data storage device of step (a) to identify homologous or non-homologous sequences; and, (c) a retrieval device for identifying said homologous or non-homologous sequences(s) of said test soybean genomic sequences of step (b). In other embodiments, at least 96 soybean genomic DNA polymorphisms identified in Table 1 or Table 3 are recorded on the computer readable medium in the computer based system. In still other embodiments, the data storage device can further comprise computer readable medium wherein phenotypic trait data from at least one of said test soybean plants is recorded thereon. The data storage device can also further comprise computer readable medium wherein data associating an allelic state with a parent, progeny, or tester soybean plant is recorded thereon. Computer based systems wherein a plurality of mapped soybean genomic DNA polymorphisms identified in Table 3 are recorded on the computer readable medium and wherein the computer readable medium further comprises genetic map location data for each of said mapped polymorphisms are also contemplated.

Isolated nucleic acid molecules for detecting polymorphisms in soybean genomic DNA identified in Table 1 and Table 3 are also provided. Isolated nucleic acid molecules for detecting a molecular marker representing a polymorphism in soybean DNA identified in Table 1 or Table 3 that comprise at least 15 nucleotides that include or are immediately adjacent to the polymorphism and are at least 90 percent identical to a sequence of the same number of consecutive nucleotides in either strand of DNA that include or are immediately adjacent to said polymorphism are contemplated. Isolated nucleic acids of the invention can further comprise a detectable label or provides for incorporation of a detectable label. The detectable label can be selected from the group consisting of an isotope, a fluorophore, an oxidant, a reductant, a nucleotide and a hapten. The detectable label can be added to the nucleic acid by a chemical reaction or incorporated by an enzymatic reaction. The isolated nucleic acid can detect a polymorphism in Table 3 selected from the group consisting of SEQ ID NO: 3122, 2914, 3984, 3608, 1448, 69, 1261, 3436, 1142, 80, 88, 980, 538, 1925, 3669, 2270, 1397, 3747, 888, 365, 2132, 1972, 459, 762, and 1094.

Other isolated oligonucleotide compositions comprising more than one isolated nucleic acid that are useful for typing the soybean polymorphisms of Table 1 or Table 3. Such isolated oligonucleotide compositions can be used to type the SNP polymorphisms by either TAQMAN® assay or Flap Endonuclease-mediated (INVADER®) assays. In one embodiment the isolated nucleic acid composition is a set of oligonucleotides comprising: (a) a pair of oligonucleotide primers wherein each of said primers comprises at least 12 contiguous nucleotides and wherein said pair of primers permit PCR amplification of a DNA segment comprising a soybean genomic DNA polymorphism locus identified in Table 1 or Table 3; and (b) at least one detector oligonucleotide that permits detection of a polymorphism in said amplified segment, wherein the sequence of said detector oligonucleotide is at least 95 percent identical to a sequence of the same number of consecutive nucleotides in either strand of a segment of soybean DNA that include or are immediately adjacent to said polymorphism of step (a). In the set of oligonucleotides, the detector oligonucleotide comprises at least 12 nucleotides and either provides for incorporation of a detectable label or further comprises a detectable label. The detectable label can be selected from the group consisting of an isotope, a fluorophore, an oxidant, a reductant, a nucleotide and a hapten. Isolated polynucleotide compositions for typing the disclosed polymorphisms with Flap Endonuclease-mediated (INVADER®) assays are also provided. Such compositions for use in Flap Endonuclease-mediated assays comprise at least two isolated nucleic acid molecules for detecting a molecular marker representing a polymorphism in soybean DNA, wherein a first nucleic acid molecule of the composition comprises an oligonucleotide that includes the polymorphic nucleotide residue and at least 8 nucleotides that are immediately adjacent to a 3' end of said polymorphic nucleotide residue, wherein a second nucleic acid molecule of the composition comprises an oligonucleotide that includes the polymorphic nucleotide residue and at least 8 nucleotides that are immediately adjacent to a 5' end of said polymorphic nucleotide residue, and wherein the polymorphism is identified in Table 1 or Table 3.

Various methods for genotyping soybean plants to select a parent plant, a progeny plant or a tester plant for breeding are also provided. In one embodiment, the method of genotyping a soybean plant to select a parent plant, a progeny plant or a tester plant for breeding comprises the steps of: a. obtaining a DNA or RNA sample from a tissue of at least one soybean plant; b. determining an allelic state of at least one soybean genomic DNA polymorphism identified in Table 1 or Table 3 for said sample from step (a), and c. using said allelic state determination of step (b) to select a parent plant, a progeny plant or a tester plant for breeding. This method of genotyping can be performed to type a mapped polymorphism identified in Table 3. The allelic state of polymorphisms can be determined by an assay permitting identification of a single nucleotide polymorphism in this genotyping method. Single nucleotide polymorphism assays used in this method can be selected from the group consisting of single base extension (SBE), allele-specific primer extension sequencing (ASPE), DNA sequencing, RNA sequencing, microarray-based analyses, universal PCR, allele specific extension, hybridization, mass spectrometry, ligation, extension-ligation, and Flap Endonuclease-mediated assays. In certain embodiments of this method, an allelic state of at least 8, at least 48, at least 96, or at least 384 distinct polymorphisms identified in Table 1 or Table 3 are determined.

The methods of genotyping can also further comprising the step of storing resultant genotype data for said one or more allelic state determinations on a computer readable medium and/or further comprise the step of comparing genotype data from one soybean plant to another soybean plant. Genotype data can also be compared to phenotypic trait data or phenotypic trait index data for at least one of said soybean plants in certain embodiments of the methods that comprise those additional steps. Genotype data can also be compared to phenotypic trait data or phenotypic trait index data for at least two of said soybean plants and determining one or more associations between said genotype data and said phenotypic trait data in certain embodiments of the methods that comprise those additional steps. In still other embodiments of methods wherein associations are determined for said phenotype trait data or phenotypic trait index data to said genotypic trait data, the genotypic trait data comprises allelic state determinations for at least 10 mapped polymorphisms identified in Table 3.

Methods of breeding soybean plants are also contemplated. The methods of breeding soybean plants comprise the steps of: (a) identifying trait values for at least one trait associated with at least two haplotypes in at least two genomic windows of up to 10 centimorgans for a breeding population of at least two soybean plants; (b) breeding two soybean plants in said breeding population to produce a population of progeny seed; (c) identifying an allelic state of at least one polymorphism identified in Table 1 or Table 3 in each of said windows in said progeny seed to determine the presence of said haplotypes; and (d) selecting progeny seed having a higher trait value for at least one trait associated with the determined haplotypes in said progeny seed, thereby breeding a soybean plant. In certain embodiments of these breeding methods, trait values are identified for at least one trait associated with at least two haplotypes in each adjacent genomic window over essentially the entirety of each chromosome. The trait value can identify a trait selected from the group consisting of herbicide tolerance, disease resistance, insect or pest resistance, altered fatty acid, protein or carbohydrate metabolism, increased grain yield, increased oil, increased nutritional content, increased growth rates, enhanced stress tolerance, preferred maturity, enhanced organoleptic properties, altered morphological characteristics, other agronomic traits, traits for industrial uses, or traits for improved consumer appeal, or a combination of traits as a multiple trait index. In other embodiments of these breeding methods, progeny seed is selected for a higher trait value for yield for a haplotype in a genomic window of up to 10 centimorgans in each chromosome. In methods where the trait value is for the yield trait and trait values are ranked for haplotypes in each window; a progeny seed can be selected which has a trait value for yield in a window that is higher than the mean trait value for yield in said window. In still other embodiments of the method, the polymorphisms in the haplotypes are in a set of DNA sequences that comprises all of the DNA sequences of SEQ ID NO: 1 through SEQ ID NO: 7800.

Methods for selecting a parent, progeny, or tester plant for breeding are also provided. These methods for selecting a parent, progeny, or tester plant for plant breeding comprise the steps of: a) determining associations between a plurality of polymorphisms identified in Table 1 or Table 3 and a plurality of traits in at least a first and a second inbred line of soybean; b) determining an allelic state of one or a plurality of polymorphism in a parent, progeny or tester plant; c) selecting the parent, progeny or tester that has a more favorable combination of associated traits. In certain embodiments, the parent, progeny or tester plant is an inbred soybean line. A favorable combination of associated traits selected in the parent, progeny or tester can be a parent, progeny or tester that provides for improved heterosis.

Methods for improving heterosis are also provided. The methods for improving heterosis comprise the steps of: (a) determining associations between a plurality of polymorphisms identified in Table 1 or Table 3 and a plurality of traits in more than two inbred lines of soybean; (b) assigning two inbred lines selected from the inbred lines of step (a) to heterotic groups, (c) making at least one cross between at least two inbred lines from step (b), wherein each inbred line comes from a distinct and complementary heterotic group and wherein the complementary heterotic groups are optimized for genetic features that improve heterosis; and (d) obtaining a hybrid progeny plant from said cross in step (c), wherein said hybrid progeny plant displays increased heterosis relative to progeny derived from a cross with an unselected inbred line.

Methods of genotyping soybean to select a parent plant, a progeny plant or a tester plant for breeding wherein a plurality of distinct sets of nucleic acids are used to type a plurality of distinct polymorphisms that map to a plurality of genomic loci are also provided. These methods of genotyping a soybean plant to select a parent plant, a progeny plant or a tester plant for breeding comprise the steps of: (a) obtaining a DNA or RNA sample from a tissue of at least one soybean plant; (b) determining an allelic state of a set of soybean genomic DNA polymorphisms comprising at least two polymorphisms identified in Table 1 or Table 3 for said sample from step (a), wherein said allelic state is determined with a set of nucleic acid molecules that provide for typing of said soybean genomic DNA polymorphisms; and c. using said allelic state determination of step (b) to select a parent plant, a progeny plant or a tester plant for breeding. However, other embodiments of the method provide for determining the allelic state of at least 5, at least 10, or at least 20 polymorphisms identified in Table 1 or Table 3. The set of soybean genomic DNA polymorphisms can comprise at least 2 polymorphisms selected from the group consisting of SEQ ID NO: 3122, 2914, 3984, 3608, 1448, 69, 1261, 3436, 1142, 80, 88, 980, 538, 1925, 3669, 2270, 1397, 3747, 888, 365, 2132, 1972, 459, 762, and SEQ ID NO: 1094. The set of soybean genomic DNA polymorphisms can also comprise at least 2 polymorphisms selected from the group consisting of SEQ ID NO: 3122, 2914, 3984, 3608, 1448, 69, 1261, 3436, 1142, and 80. Alternatively, the soybean genomic DNA polymorphisms can also comprise at least 2 polymorphisms selected from the group consisting of SEQ ID NO: 3122, 2914, 3984, 3608, and 1448. In one embodiment, the set of soybean genomic polymorphisms comprise the polymorphisms SEQ ID NO: 3122 and SEQ ID NO: 2914. In this method, the set of soybean genomic DNA polymorphisms can be associated with a trait values identified for at least one of yield, lodging, maturity, plant height, drought tolerance and cold germination. Genotyping methods where the set of soybean genomic DNA polymorphisms are associated with a trait value for yield are particularly contemplated. In one embodiment, the polymorphisms associated with a trait value are selected from the group consisting of SEQ ID NO: 3122, 2914, 3984, 3608, 1448, 69, 1261, 3436, 1142, 80, 88, 980, 538, 1925, 3669, 2270, 1397, 3747, 888, 365, 2132, 1972, 459, 762, and SEQ ID NO: 1094. Polymorphisms selected from the group consisting of SEQ ID NO: 3122, 2914, 3984, 3608, 1448, 69, 1261, 3436, 1142, 80, 88, 980, 538, 1925, 3669, 2270, 1397, 3747, 888, 365, 2132, 1972, 459, 762, and SEQ ID NO: 1094 are associated with a trait value for yield.

Methods of genotyping soybean to select a parent plant, a progeny plant or a tester plant for breeding wherein a plurality of distinct sets of nucleic acids are used to type a plurality of distinct polymorphisms that map to a plurality of genomic loci distributed across the genome of soybean are also provided. In these methods, a set of at least 20 soybean genomic DNA polymorphisms identify polymorphisms that are distributed across the genome of soybean are typed. In certain embodiments of this method, the set of at least 20 soybean genomic DNA polymorphisms that are typed identify polymorphisms that are distributed across a single chromosome of soybean or are distributed across at least two chromosomes of soybean. In still other embodiments of this method, the set of at least 20 soybean genomic DNA polymorphisms identify polymorphisms that are distributed across all chromosomes of soybean. When the 20 soybean genomic DNA polymorphisms are distributed across all chromosomes of soybean, they can be distributed such that at least 1 of the polymorphisms in the set maps to each chromosome such that at least 1 of said polymorphisms in said set maps to each chromosome. However, this method can also employ more polymorphisms, such that at least 10 of the soybean genomic DNA polymorphisms in the set map to each chromosome. In other embodiments, at least 20 or at least 50 of the soybean genomic DNA polymorphisms in the set map to each chromosome. In certain embodiments of the methods, at least one polymorphism maps to chromosome 1 and can be selected from the group consisting of SEQ ID NO: 4093, 3168, 1993, 4808, 5176, 3705, 2968, 6401, 7154, 7741, 177, 4251, 584, 4672, 4078, 3248, 2471, 1728, 4140, 4169, 4258, 1466, 5899, 4203, 3624, 6068, 6303, 6309, 3363, 6057, 2579, 6431, 2744, 3018, 6670, 3133, 4591, 4656, 3127, 4306, 2161, 6021, 3623, 6504, 1612, 516, 4296, 2702, 4124, 1076, 967, 3885, 800, 2153, 5915, 7766, 6672, 5391, 2645, 382, 1550, 5564, 1763, 7566, 1722, 3327, 3724, 6359, 1499, 6680, 1147, 345, 1832, 608, 7548, 4553, 5482, 7055, 2157, 3270, 6896, 7347, 1502, 1765, 4173, 6150, 5085, 2607, 6686, 448, 2355, 2639, 4850, and 1897.

In other embodiments of the method, at least one polymorphism maps to chromosome 2 is selected from the group consisting of SEQ ID NO: 2484, 3849, 6346, 6230, 336, 2253, 4062, 5763, 6118, 1450, 4299, 4268, 7480, 7774, 3664, 261, 4018, 2265, 5833, 933, 7547, 1519, 3271, 4754, 7691, 1349, 5587, 6852, 6500, 7429, 4261, 3359, 6845, 1560, 4977, 1626, 4440, 2019, 2164, 690, 2491, 3242, 5314, 7053, 3747, 6728, 389, 3986, 1485, 1988, 5472, 6494, 4023, 221, 5566, 4602, 6519, 2042, 1181, 2514, 3199, 1462, 904, 7515, 329, 1377, 6130, and 2194.

In other embodiments of the method, at least one polymorphism maps to chromosome 3 is selected from the group consisting of SEQ ID NO: 2222, 1105, 4825, 1773, 5419, 3275, 3562, 4148, 6154, 3488, 3349, 7710, 3721, 4423, 1313, 3801, 3103, 4222, 2910, 2504, 3730, 3834, 6625, 355, 5025, 4164, 2260, 6368, 2022, 3567, 2957, 3362, 359, 6180, 2070, 5380, 917, 6320, 5213, 1186, 1616, 6539, 7191, 5055, 7378, 1269, 7380, 1986, 2274, 5838, 6098, 3758, 1280, 6022, 6977, 6783, 3060, 6560, 5330, 1630, 2966, 2166, 5858, 7297, 2650, 6467, 1075, and 6910.

In other embodiments of the method, at least one polymorphism maps to chromosome 4 is selected from the group consisting of SEQ ID NO: 5919, 631, 6047, 6592, 283, 6474, 4015, 1740, 3995, 3756, 5255, 2341, 2933, 292, 3984, 5538, 3157, 6439, 368, 1082, 7360, 2108, 2629, 362, 4489, 4980, 5522, 463, 163, 5923, 6020, 1995, 6388, 1151, 3463, 5658, 443, 5236, 2637, 3238, 1950, 2824, 3674, 5762, 3210, 7511, 2842, 2319, 4531, 2883, 2225, 4816, 892, 7386, 4509, 5846, 823, 3797, 3024, 3746, 7637, 4171, 4257, 2622, 6249, 950, 4156, 3339, 3717, 976, 1161, 5885, 1099, 1533, 1827, 4787, 360, and 4221.

In other embodiments of the method, at least one polymorphism maps to chromosome 5 is selected from the group consisting of SEQ ID NO: 5225, 5448, 6261, 1464, 753, 5766, 6067, 4519, 4809, 6745, 6451, 3594, 7734, 2884, 4032, 88, 5977, 1880, 4394, 517, 1611, 2963, 1582, 7292, 7181, 4255, 2659, 3217, 2736, 2638, 2437, 2912, 1197, 6684, 2810, 5175, 7009, 1623, 6510, 4346, 6239, 2320, 3905, 5458, 4072, 4318, 6367, 4001, 2079, 1319, 3691, 6632, 3315, 3391, 4117, 6191, 5002, 1223, 1261, 4146, 2417, 3963, 1090, 6295, 6793, 2878, 5198, 3512, 2407, 3533, 1448, 7152, 69, 3539, 5172, 5468, 5602, 3273, 3692, 6691, 6121, 2743, 4289, 4044, 1837, 486, 1465, 2050, 4125, 5105, 3481, 4281, 1257, 2307, 739, 5372, 1513, 4652, 7200, 1589, 2188, 1951, 2292, 6241, 6516, 4185, 202, 1748, 4580, 1183, 5642, 6955, 4986, 6848, 98, 2099, 7112, 3402, 3530, 5384, 3827, 1420, 311, 817, and 5169.

In other embodiments of the method, at least one polymorphism maps to chromosome 6 is selected from the group consisting of SEQ ID NO: 1920, 2270, 2334, 811, 3328, 5137, 1590, 1286, 1918, 5009, 5108, 4798, 2032, 2186, 2803, 5141, 2954, 805, 750, 1037, 7529, 1310, 5854, 771, 244, 2733, 5634, 6488, 4812, 5101, 7767, 7206, 7539, 6432, 4861, 3470, 3454, 3653, 6314, 1427, 4232, 4100, 4757, 278, 1969, 4604, 1813, 4436, 5239, 7454, 4998, 2325, 6203, 4077, 1829, 4069, 6655, 2657, 3593, 7455, 6, 10, 199, 6264, 4050, 6189, 7383, 2123, 5288, 5305, 89, 149, 6194, 4849, 1963, 3839, 5573, 1493, 824, 3645, 704, 1404, 980, 7371, 3709, 5459, 6413, 3784, 1309, 5882, 1379, 3547, 3903, 1646, 973, 2176, 2515, 2762, 900, 1027, 3872, 5916, 6311, 3180, 7535, 4696, 7492, 514, 4360, 860, 1917, 3392, and 3433.

In other embodiments of the method, at least one polymorphism maps to chromosome 7 is selected from the group consisting of SEQ ID NO: 7333, 7600, 481, 4994, 2982, 1106, 7136, 4949, 1998, 5755, 2429, 3471, 2155, 4852, 5661, 7516, 5406, 5539, 5266, 5320, 4418, 3619, 172, 4614, 780, 5951, 1410, 4348, 5572, 5708, 6304, 4215, 912, 6548, 1883, 469, 4202, 1996, 602, 5656, 144, 2221, 79, 7271, 6351, 3879, 504, 2731, 1191, 2377, 2333, 3040, 3023, 255, 1258, 2858, 5021, 4500, 2761, 5737, 7012, 2445, 873, 6300, 332, 2241, 1509, 592, 1571, 4076, 6360, 6398, 2569, 154, 5723, 3389, 161, 153, 398, 1558, 3056, 3714, 3775, 6023, 1542, 2741, 6746, 7785, 5509, 1312, 3941, 7247, 6148, 1625, 4210, 7192, 3929, 2886, and 4944.

In other embodiments of the method, at least one polymorphism maps to chromosome 8 is selected from the group consisting of SEQ ID NO: 3125, 4896, 5102, 2536, 1028, 1642, 5457, 2386, 5357, 4147, 6035, 2644, 3013, 6491, 4142, 5787, 1819, 7259, 4128, 612, 215, 6681, 2786, 6766, 6483, 5795, 2734, 4727, 115, 654, 1551, 1038, 1414, 2353, 2330, 47, 1816, 1231, 2915, 2143, 972, 2698, 4029, 4597, 1575, 5161, 2466, 3358, 2173, 5192, 832, 2354, 2008, 6639, 6110, 3410, 5729, 6995, 2214, 585, 7509, 1878, 4822, 1237, 3813, 3829, 5555, 3962, 840, 6215, 4705, 1884, 218, 809, 7033, 2282, 5929, 168, 6006, 429, 2509, 424, 7408, 3817, 3002, 3259, 7134, 1069, 6428, 2990, 7180, 3497, 5792, 1706, 6032, 3432, 3431, and 4823.

In other embodiments of the method, at least one polymorphism maps to chromosome 9 is selected from the group consisting of SEQ ID NO: 6190, 174, 2779, 5185, 5698, 6454, 2531, 50, 5080, 4964, 2739, 4668, 2588, 849, 7087, 3975, 3977, 6717, 7375, 2804, 4448, 2525, 1546, 1834, 6863, 4971, 1129, 6095, 6287, 5961, 6931, 6935, 3461, 2424, 2409, 1972, 2974, 1906, 553, 661, 792, 4842, 5817, 150, 4492, 2231, 2956, 4231, 2851, 4160, 1598, 3767, 6721, 6370, 7316, 3787, 3156, 1033, 2821, 6980, 3656, 3269, 4797, 6269, 4275, 7185, 6034, 4538, 7096, 3377, 3409, 1620, 487, 6615, 4941, 7419, 6685, 7504, 6281, 6734, 4847, 7127, 4663, 1520, 1905, 3129, 1296, 4014, 2312, 4935, 1239, 3151, 5149, 6908, 5431, 3161, and 6589.

In other embodiments of the method, at least one polymorphism maps to chromosome 10 is selected from the group consisting of SEQ ID NO: 2434, 2678, 920, 6861, 6464, 6950, 1786, 1567, 2899, 5920, 3251, 3049, 1112, 6008, 7346, 611, 3203, 1992, 6335, 587, 3093, 459, 909, 4437, 2506, 4920, 4786, 6518, 6927, 4751, 1138, 3263, 3311, 4226, 3719, 3865, 4948, 2894, 6174, 6659, 3371, 3089, 5513, 4646, 4381, 2055, 2217, 2939, 2717, 5744, 3262, 7681, 7411, 5215, 7761, 2713, 2061, 4298, 6244, 1149, 4046, 4701, 5243, 4784, 3140, 7173, 407, 4081, 6478, 509, 1389, 3590, 2508, 835, 7224, 1785, 1757, 3464, 6202, 6700, 4857, 3167, 5146, 7615, 7790, and 5439.

In other embodiments of the method, at least one polymorphism maps to chromosome 11 is selected from the group consisting of SEQ ID NO: 1531, 4150, 4186, 5997, 6107, 5692, 1032, 6449, 1432, 12, 600, 1067, 353, 5549, 3757, 2136, 7341, 5727, 3491, 55, 449, 6936, 5191, 538, 3372, 3694, 5665, 5754, 3755, 7295, 3572, 2237, 7794, 1624, 2800, 3876, 337, 7203, 4953, 300, 1326, 5480, 4024, 3898, 507, 3939, 6045, 5364, 4039, 3820, 53, 7315, 7340, 1172, 2530, 6395, 4821, 6009, 2843, 3037, 5297, 4562, 4096, 3828, 2533, 6658, and 7084.

In other embodiments of the method, at least one polymorphism maps to chromosome 12 is selected from the group consisting of SEQ ID NO: 4218, 4178, 4434, 5076, 1436, 216, 7176, 4295, 7085, 5299, 3663, 2121, 1329, 5659, 3420, 2057, 4011, 1085, 3255, 3062, 6668, 2559, 852, 3809, 135, 5694, 182, 4127, 2944, 6902, 206, 4287, 4569, 2610, 2699, 2685, 3738, 7293, 5709, 2697, 7155, 1351, 5531, 3733, 5663, 6001, 7470, 7486, 1196, 4405, 755, 5608, 7092, 2281, 2608, 6358, 6787, 6005, 70, 2680, 14, 5154, 5639, 4600, 7195, 6688, 3780, 3892, 4428, 6120, 5415, 322, 1820, and 326.

In other embodiments of the method, at least one polymorphism maps to chromosome 13 is selected from the group consisting of SEQ ID NO: 2647, 7207, 1605, 2888, 6147, 1956, 3979, 4715, 7262, 5461, 3524, 948, 6557, 5346, 6342, 5847, 73, 1268, 4278, 4385, 4259, 4968, 1898, 7731, 3710, 5434, 5508, 1944, 7448, 5031, 7614, 6568, 583, 7246, 762, 3390, 6069, 5142, 269, 1203, 1591, 1946, 1442, 126, 1925, 3696, 4198, 370, 1169, 1780, 5336, 1142, 2489, 5443, 5626, 7153, 1363, 1476, 3183, 893, 7526, 5826, 3920, 3114, 7321, 7339, 493, 1059, 4745, 5515, 6339, 3011, 4796, 6622, 4175, 4240, 2801, 267, 2565, 3522, 6169, 1079, 4802, 885, 910, 2970, 5745, 2980, 7472, 5491, 598, 2494, 5561, 6750, 6198, 7184, 86, 2695, 721, 773, 508, 7487, 879, 3030, 3408, 348, 7559, 1463, 991, 7253, 184, 2877, 72, 4315, 5033, 2327, 7304, 107, 3659, 2413, 6073, 3110, 7072, 4552, 5976, 4441, 6475, 2519, 3174, 4576, 6716, 3333, 5619, 6458, 123, 1396, and 4130.

In other embodiments of the method, at least one polymorphism maps to chromosome 14 is selected from the group consisting of SEQ ID NO: 2240, 2749, 1847, 2950, 5924, 6509, 1246, 4790, 5893, 5855, 4608, 2485, 5127, 1599, 4990, 2790, 4615, 6767, 7714, 7659, 543, 1267, 2560, 6858, 350, 3187, 3330, 6588, 1684, 395, 6081, 6809, 726, 297, 1071, 1749, 6730, 1811, 2724, 3435, 4993, 5074, 3436, 6792, 2297, 489, 4535, 3897, 3608, 908, 1835, 4249, 4685, 5895, 1855, 4, 8, 5059, 7105, 4269, 7556, 3101, 1525, 3367, 6143, 6084, and 5147.

In other embodiments of the method, at least one polymorphism maps to chromosome 15 is selected from the group consisting of SEQ ID NO: 868, 7416, 3126, 3298, 5695, 3227, 1182, 4568, 1697, 2703, 6786, 80, 7387, 4742, 3597, 6593, 6197, 6666, 1093, 2708, 3844, 7066, 3574, 944, 4560, 1730, 5743, 2020, 601, 3646, 5610, 795, 1566, 3919, 5666, 7049, 7690, 6421, 7349, 3355, 1431, 51, 2021, 3303, 3144, 1094, 5277, 3800, 120, 139, 2864, 6899, 4659, 6983, 7056, 2920, 201, 1087, 5056, 446, 6077, 4507, 4276, 712, 441, 2718, 4153, 2385, 3117, 7723, 5908, 3123, 3016, 4262, 1999, 2601, 2555, 1324, 5257, 6830, 3459, 4293, 4458, 6673, 4277, and 3184.

In other embodiments of the method, at least one polymorphism maps to chromosome 16 is selected from the group consisting of SEQ ID NO: 6550, 826, 1298, 2636, 7555, 7284, 7278, 2051, 2860, 723, 7324, 1205, 3200, 1581, 2403, 5094, 3039, 5261, 4426, 4703, 3906, 25, 4598, 1282, 5802, 6687, 1885, 4570, 3917, 3185, 4115, 5957, 6268, 250, 1225, 3393, 1644, 3846, 4380, 1708, 650, 1260, 3348, 3606, 5011, 7641, 5436, 4392, 5836, 7661, 452, 7015, 4522, 1498, 1473, 929, 4040, 6294, 2777, 2387, 1675, 1361, 3034, 1482, 3193, 7330, 3283, 7450, 1515, 5254, 4074, 3218, 622, 6055, 808, 916, 2367, 6489, 6591, 4245, 253, 7572, 2029, 5462, and 5421.

In other embodiments of the method, at least one polymorphism maps to chromosome 17 is selected from the group consisting of SEQ ID NO: 1394, 2246, 2662, 3716, 2458, 4814, 1863, 2289, 5952, 2905, 4952, 396, 7078, 4188, 5442, 4163, 4871, 317, 5321, 6094, 7656, 4831, 3, 5985, 3261, 273, 4005, 1511, 6172, 7394, 4463, 1158, 1354, 1769, 2118, 2191, 3076, 4880, 5015, 5881, 6391, 7400, 720, 1100, 915, 7051, 118, 4135, 7109, 2914, 2975, 3249, 3352, 1288, 1405, 5637, 7290, 5914, 7631, 3669, 2001, 3899, 1761, 5677, 5680, 992, 3806, 4158, 3540, 2675, 3122, 7301, 7303, 7797, 6959, 7343, 1359, 6165, 1018, 6562, 2881, 4303, 6537, 416, 5424, 249, 3864, 955, 2859, 1900, 6653, 841, 7129, 542, 2400, 5664, 4965, 638, 7327, and 3368.

In other embodiments of the method, at least one polymorphism maps to chromosome 18 is selected from the group consisting of SEQ ID NO: 2595, 2802, 3882, 1872, 7029, 1141, 7208, 6619, 6803, 7175, 7183, 3928, 5774, 5890, 7228, 6046, 2523, 3350, 2535, 7244, 3519, 7099, 259, 6981, 1561, 2052, 3163, 1226, 3228, 6541, 4667, 425, 6052, 5742, 2623, 7167, 1425, 3059, 888, 6301, 365, 502, 4355, 3991, 2958, 5167, 2299, 7131, 7613, 7257, 6748, 2856, 4384, 550, 1658, 4216, 7665, 3356, 6389, 4386, 414, 3149, 1572, 7361, 7279, 7296, 205, 3947, 162, 3508, and 734.

In other embodiments of the method, at least one polymorphism maps to chromosome 19 is selected from the group consisting of SEQ ID NO: 3545, 1664, 6958, 3499, 7622, 2562, 3361, 191, 2084, 1472, 1140, 5208, 3690, 7735, 6455, 3830, 7323, 848, 2890, 5913, 1413, 2953, 2017, 1335, 7226, 3722, 1887, 3398, 313, 1136, 7064, 7490, 4182, 4133, 1933, 3788, 1340, 2025, 4378, 3625, 2456, 3650, 1484, 7232, 4179, 4236, 5401, 7094, 7635, 6850, 7471, 6507, 6514, 4710, 4497, 1369, 4327, 2846, 5685, 197, 1146, 2189, 7017, 1378, 4792, 1047, 1397, 5939, 2291, 4151, 613, 488, 7080, 5481, 1017, 1529, 2012, 5832, 2132, 2976, 3910, 2538, 5416, 2380, 6138, 4872, 2065, 1628, 7157, 6481, 3299, 6242, and 4960.

In other embodiments of the method, at least one polymorphism maps to chromosome 20 is selected from the group consisting of SEQ ID NO: 3967, 845, 3229, 5398, 2348, 3671, 3592, 5747, 5987, 3742, 1164, 6754, 1364, 6380, 3785, 6667, 4242, 175, 1979, 116, 3950, 166, 3026, 3859, 3682, 1784, 3869, 1062, 3837, 499, 7023, 539, 6232, 192, 4057, 1922, 2371, 5361, 1219, 5786, 7190, 3208, 1544, 3321, 3306, 2104, 4490, 6026, 2149, 4730, 4746, 4105, 1991, 3058, 2895, 5331, 6581, 2651, 4954, 4273, 4045, 1297, 231, 1044, 1249, 1908, 1128, 2516, 6135, 3414, 6709, 6708, 1725, 7196, 3266, 1202, 1576, 6290, 7201, and 3665.

Further features and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings:

FIGS. 1A-1B are genetic maps of soybean showing the density of mapped polymorphisms of this invention.

FIG. 2 is an allelogram illustrating results of a genotyping assay.

DEFINITIONS

Figure 1B:
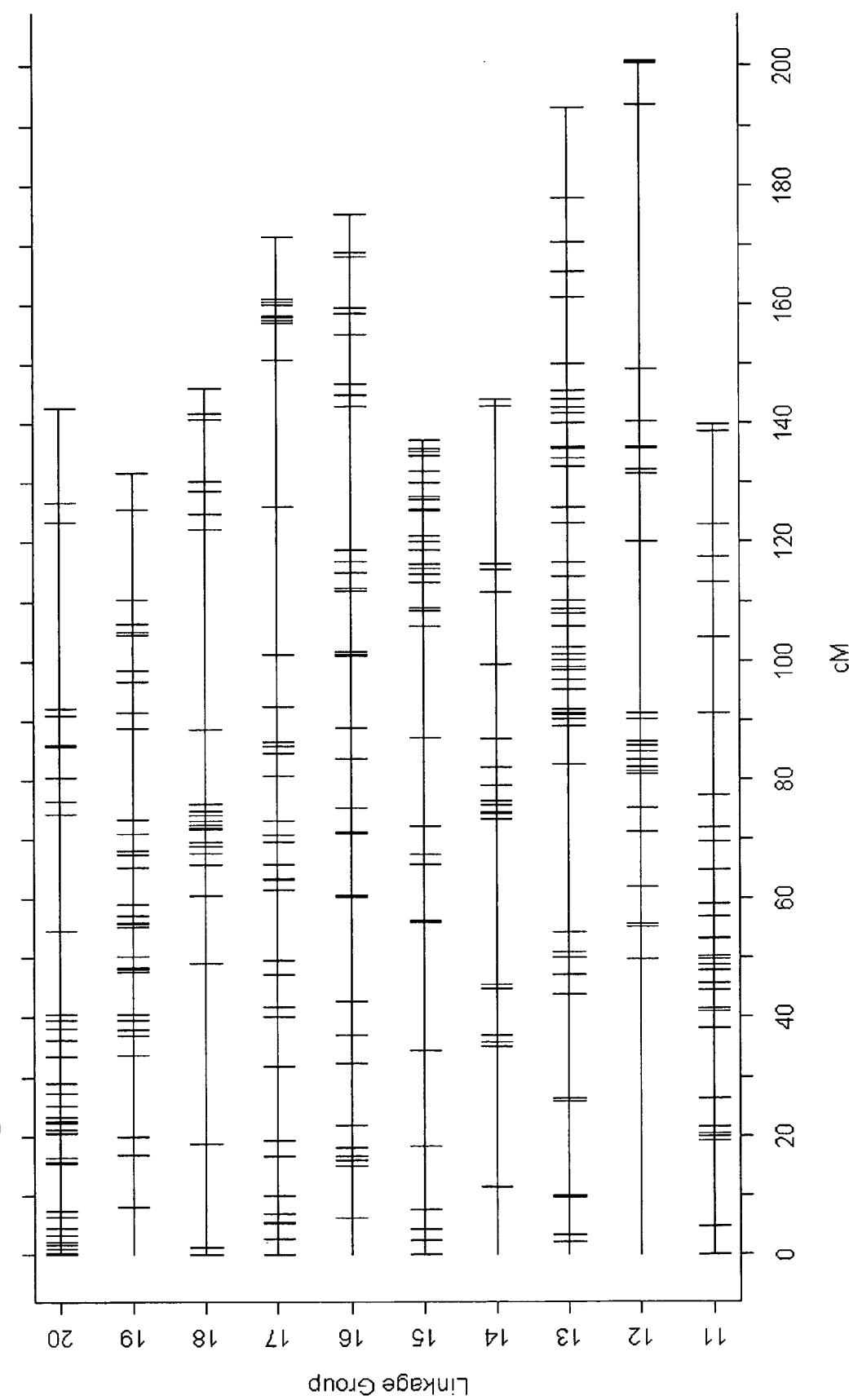

As used herein certain terms and phrases are defined as follows.

An "allele" refers to an alternative sequence at a particular locus; the length of an allele can be as small as 1 nucleotide base, but is typically larger. Allelic sequence can be amino acid sequence or nucleic acid sequence. A "locus" is a short sequence that is usually unique and usually found at one particular location in the genome by a point of reference; e.g., a short DNA sequence that is a gene, or part of a gene or intergenic region. A locus of this invention can be a unique PCR product at a particular location in the genome. The loci of this invention comprise one or more polymorphisms; i.e., alternative alleles present in some individuals.

An "allelic state" refers to the nucleic acid sequence that is present in a nucleic acid molecule that contains a genomic polymorphism. For example, the nucleic acid sequence of a DNA molecule that contains a single nucleotide polymorphism may comprise an A, C, G, or T residue at the polymorphic position such that the allelic state is defined by which residue is present at the polymorphic position. For example, the nucleic acid sequence of an RNA molecule that contains a single nucleotide polymorphism may comprise an A, C, G, or U residue at the polymorphic position such that the allelic state is defined by which residue is present at the polymorphic position. Similarly, the nucleic acid sequence of a nucleic acid molecule that contains an Indel may comprise an insertion or deletion of nucleic acid sequences at the polymorphic position such that the allelic state is defined by the presence or absence of the insertion or deletion at the polymorphic position.

An "association", when used in reference to a polymorphism and a phenotypic trait or trait index, refers to any statistically significant correlation between the presence of a given allele of a polymorphic locus and the phenotypic trait or trait index value, wherein the value may be qualitative or quantitative.

A "distinct set of nucleic acid molecules" refers to one or more nucleic acid molecules that hybridize to DNA sequences that are include, are immediately adjacent to, or are within about 1000 base pairs of either the 5' or 3' end of a given soybean genomic polymorphism. In certain embodiments, the distinct set of nucleic acid molecules will comprise a single nucleic acid sequence that includes or is immediately adjacent to a given polymorphism. In other embodiments, the distinct set of nucleic acid molecules will comprise one or more nucleic acid sequences that include or are immediately adjacent to the polymorphism as well as other nucleic acid sequences that are within about 1000 base pairs of either the 5' or 3' end of the polymorphism.

"Genotype" refers to the specification of an allelic composition at one or more loci within an individual organism. In the case of diploid organisms, there are two alleles at each locus; a diploid genotype is said to be homozygous when the alleles are the same, and heterozygous when the alleles are different.

"Haplotype" refers to an allelic segment of genomic DNA that tends to be inherited as a unit; such haplotypes can be characterized by one or more polymorphic molecular markers and can be defined by a size of not greater than 10 centimorgans. With higher precision provided by a higher density of polymorphisms, haplotypes can be characterized by genomic windows, for example, in the range of 1-5 centimorgans.

The phrase "immediately adjacent", when used to describe a nucleic acid molecule that hybridizes to DNA containing a polymorphism, refers to a nucleic acid that hybridizes to DNA sequences that directly abut the polymorphic nucleotide base position. For example, a nucleic acid molecule that can be used in a single base extension assay is "immediately adjacent" to the polymorphism.

"Interrogation position" refers to a physical position on a solid support that can be queried to obtain genotyping data for one or more predetermined genomic polymorphisms.

"Consensus sequence" refers to a constructed DNA sequence which identifies SNP and Indel polymorphisms in alleles at a locus. Consensus sequence can be based on either strand of DNA at the locus and states the nucleotide base of either one of each SNP in the locus and the nucleotide bases of all Indels in the locus. Thus, although a consensus sequence may not be a copy of an actual DNA sequence, a consensus sequence is useful for precisely designing primers and probes for actual polymorphisms in the locus.

"Phenotype" refers to the detectable characteristics of a cell or organism which are a manifestation of gene expression.

"Phenotypic trait index" refers to a composite value for at least two phenotypic traits, wherein each phenotypic trait may be assigned a weight to reflect relative importance for selection.

A "marker" or "molecular marker" as used herein is a DNA sequence (e.g. a gene or part of a gene) exhibiting polymorphism between two or more plants of the same species, which can be identified or typed by a simple assay. Useful polymorphisms include a single nucleotide polymorphisms (SNPs), insertions or deletions in DNA sequence (Indels), single feature polymorphisms (SFPs), and simple sequence repeats of DNA sequence (SSRs).

"Marker Assay" refers to a method for detecting a polymorphism at a particular locus using a particular method. Methods for detecting polymorphisms include, but are not limited to, restriction fragment length polymorphism (RFLP), single base extension, electrophoresis, sequence alignment, allelic specific oligonucleotide hybridization (ASO), RAPD, allele-specific primer extension sequencing (ASPE), DNA sequencing, RNA sequencing, microarray-based analyses, universal PCR, allele specific extension, hybridization, mass spectrometry, ligation, extension-ligation, endonuclease-mediated dye release assays and Flap Endonuclease-mediated assays. Exemplary single base extension assays are disclosed in U.S. Pat. No. 6,013,431. Exemplary endonuclease-mediated dye release assays for allelic state determination of SNPs where an endonuclease activity releases a reporter dye from a hybridization probe are disclosed in U.S. Pat. No. 5,538,848.

"Linkage" refers to relative frequency at which types of gametes are produced in a cross. For example, if locus A has genes "A" or "a" and locus B has genes "B" or "b" and a cross between parent I with AABB and parent B with aabb will produce four possible gametes where the genes are segregated into AB, Ab, aB and ab. The null expectation is that there will be independent equal segregation into each of the four possible genotypes, i.e. with no linkage ¼ of the gametes will of each genotype. Segregation of gametes into a genotypes differing from ¼ are attributed to linkage.

"Linkage disequilibrium" is defined in the context of the relative frequency of gamete types in a population of many individuals in a single generation. If the frequency of allele A is p, a is p', B is q and b is q', then the expected frequency (with no linkage disequilibrium) of genotype AB is pq, Ab is pq', aB is p' q and ab is p' q'. Any deviation from the expected frequency is called linkage disequilibrium. Two loci are said to be "genetically linked" when they are in linkage disequilibrium.

"Quantitative Trait Locus (QTL)" refers to a locus that controls to some degree traits that are usually continuously distributed and which can be represented quantitatively.

As used herein "sequence identity" refers to the extent to which two optimally aligned polynucleotide or peptide sequences are invariant throughout a window of alignment of components, e.g. nucleotides or amino acids. An "identity fraction" for aligned segments of a test sequence and a reference sequence is the number of identical components which are shared by the two aligned sequences divided by the total number of components in reference sequence segment, i.e. the entire reference sequence or a smaller defined part of the reference sequence. "Percent identity" is the identity fraction times 100.

As used herein, "typing" refers to any method whereby the specific allelic form of a given soybean genomic polymorphism is determined. For example, a single nucleotide polymorphism (SNP) is typed by determining which nucleotide is present (i.e. an A, G, T, or C). Insertion/deletions (Indels) are determined by determining if the Indel is present. Indels can be typed by a variety of assays including, but not limited to, marker assays.

DETAILED DESCRIPTION OF THE PREFERRED EMBODIMENTS

The following detailed description relates to the isolated nucleic acid compositions and related methods for genotyping soybean plants. In general, these compositions and methods can be used to genotype soybean plants from the genus *Glycine*. More specifically, soybean plants from the species *Glycine max* and the subspecies *Glycine max* L. ssp. *max* or *Glycine max* ssp. *formosana* can be genotyped using these compositions and methods. In an additional aspect, the soybean plant is from the species *Glycine soja*, otherwise known as wild soybean, can be genotyped using these compositions and methods. Alternatively, soybean germplasm derived from any of *Glycine max, Glycine max* L. ssp. *max, Glycine max* ssp. *Formosana*, and/or *Glycine soja* can be genotyped using compositions and methods provided herein.

Isolated Nucleic Acid Molecules—Loci, Primers and Probes

The soybean loci of this invention comprise a series of molecular markers which comprises at least 20 consecutive nucleotides and includes or is adjacent to one or more polymorphisms identified in Table 1 or Table 3. Such soybean loci have a nucleic acid sequence having at least 90% sequence identity, more preferably at least 95% or even more preferably for some alleles at least 98% and in many cases at least 99% sequence identity, to the sequence of the same number of nucleotides in either strand of a segment of soybean DNA which includes or is adjacent to the polymorphism. The nucleotide sequence of one strand of such a segment of soybean DNA may be found in a sequence in the group consisting of SEQ ID NO: 1 through SEQ ID NO: 7800. It is understood by the very nature of polymorphisms that for at least some alleles there will be no identity to the disclosed polymorphism, per se. Thus, sequence identity can be determined for sequence that is exclusive of the disclosed polymorphism sequence. In other words, it is anticipated that additional alleles for the polymorphisms disclosed herein may exist, can be easily characterized by sequencing methods, and can be used for genotyping. For example, one skilled in the art will appreciate that for a single nucleotide polymorphism where just two polymorphic residues are disclosed (e.g. an "A" or a "G") can also comprise other polymorphic residues (e.g. a "T" and/or a "G").

The polymorphisms in each locus are identified more particularly in Table 1 or Table 3. SNPs are particularly useful as genetic markers because they are more stable than other classes of polymorphisms and are abundant in the soybean genome. SNPs can result from insertions, deletions, and point mutations. In the present invention a SNP can represent a single indel event, which may consist of one or more base pairs, or a single nucleotide polymorphism. Polymorphisms shared by two or more individuals can result from the individuals descending from a common ancestor. This "Identity by descent" (IBD) characterizes two loci/segments of DNA that are carried by two or more individuals and were all derived from the same ancestor. "Identity by state" (IBS) characterizes two loci/segments of DNA that are carried by two or more individuals and have the same observable alleles at those loci. When a large set of crop lines is considered, and multiple lines have the same allele at a marker locus, it is necessary to ascertain whether IBS at the marker locus is a reliable predictor of IBD at the chromosomal region surrounding the marker locus. A good indication that a number of marker loci in a segment are enough to characterize IBD for the segment is that they can predict the allele present at other marker loci within the segment. The stability and abundance of SNPs in addition to the fact that they rarely arise independently makes them useful in determining IBD.

For many genotyping applications it is useful to employ as markers polymorphisms from more than one locus. Thus, one aspect of the invention provides a collection of nucleic acid molecules that permit typing of polymorphisms of different loci. The number of loci in such a collection can vary but will be a finite number, e.g. as few as 2 or 5 or 10 or 25 loci or more, for instance up to 40 or 75 or 100 or more loci.

Another aspect of the invention provides isolated nucleic acid molecules which are capable of hybridizing to the polymorphic soybean loci of this invention. In certain embodiments of the invention, e.g. which provide PCR primers, such molecules comprise at least 15 nucleotide bases. Molecules useful as primers can hybridize under high stringency conditions to a one of the strands of a segment of DNA in a polymorphic locus of this invention. Primers for amplifying DNA are provided in pairs, i.e. a forward primer and a reverse primer. One primer will be complementary to one strand of DNA in the locus and the other primer will be complementary to the other strand of DNA in the locus, i.e. the sequence of a primer is preferably at least 90%, more preferably at least 95%, identical to a sequence of the same number of nucleotides in one of the strands. It is understood that such primers can hybridize to sequence in the locus which is distant from the polymorphism, e.g. at least 5, 10, 20, 50, 100, 200, 500 or up to about 1000 nucleotide bases away from the polymorphism. Design of a primer of this invention will depend on factors well known in the art, e.g. avoidance or repetitive sequence.

Another aspect of the isolated nucleic acid molecules of this invention are hybridization probes for polymorphism assays. In one aspect of the invention such probes are oligonucleotides comprising at least 12 nucleotide bases and a detectable label. The purpose of such a molecule is to hybridize, e.g. under high stringency conditions, to one strand of DNA in a segment of nucleotide bases which includes or is adjacent to the polymorphism of interest in an amplified part of a polymorphic locus. Such oligonucleotides are preferably at least 90%, more preferably at least 95%, identical to the sequence of a segment of the same number of nucleotides in one strand of soybean DNA in a polymorphic locus. The detectable label can be a radioactive element or a dye. In preferred aspects of the invention, the hybridization probe further comprises a fluorescent label and a quencher, e.g. for use hybridization probe assays of the type known as TAQ-MAN® assays, available from AB Biosystems.

Isolated nucleic acid molecules of the present invention are capable of hybridizing to other nucleic acid molecules including, but not limited, to soybean genomic DNA, cloned soybean genomic DNA, and amplified soybean genomic DNA under certain conditions. As used herein, two nucleic acid molecules are said to be capable of hybridizing to one another if the two molecules are capable of forming an anti-parallel, double-stranded nucleic acid structure. A nucleic acid molecule is said to be the "complement" of another nucleic acid molecule if they exhibit "complete complementarity" i.e. each nucleotide in one sequence is complementary to its base pairing partner nucleotide in another sequence. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Nucleic acid molecules which hybridize to other nucleic acid molecules, e.g. at least under low stringency conditions are said to be "hybridizable cognates" of the other nucleic acid molecules. Conventional stringency conditions are described by Sambrook et al., Molecular Cloning, A Laboratory Manual, 2nd Ed., Cold Spring Harbor Press, Cold Spring Harbor, N.Y. (1989) and by Haymes et al., Nucleic Acid Hybridization, A Practical Approach, IRL Press, Washington, D.C. (1985), each of which is incorporated herein by reference. Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1-6.3.6, incorporated herein by reference. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In a preferred embodiment, a nucleic acid molecule of the present invention will specifically hybridize to one strand of a segment of soybean DNA having a nucleic acid sequence as set forth in SEQ ID NO: 1 through SEQ ID NO: 7800 under moderately stringent conditions, for example at about 2.0× SSC and about 65° C., more preferably under high stringency conditions such as 0.2×SSC and about 65° C.

For assays where the molecule is designed to hybridize adjacent to a polymorphism which is detected by single base extension, e.g. of a labeled dideoxynucleotide, such molecules can comprise at least 15, more preferably at least 16 or 17, nucleotide bases in a sequence which is at least 90 percent, preferably at least 95%, identical to a sequence of the same number of consecutive nucleotides in either strand of a segment of polymorphic soybean DNA. Oligonucleotides for single base extension assays are available from Orchid Biosystems.

Isolated nucleic acid molecules useful as hybridization probes for detecting a polymorphism in soybean DNA can be designed for a variety of assays. For assays, where the probe is intended to hybridize to a segment including the polymorphism, such molecules can comprise at least 12 nucleotide bases and a detectable label. The sequence of the nucleotide bases is preferably at least 90 percent, more preferably at least 95%, identical to a sequence of the same number of consecutive nucleotides in either strand of a segment of soybean DNA in a polymorphic locus of this invention. The detectable label is a dye at one end of the molecule. In preferred aspects the isolated nucleic acid molecule comprises a dye and dye quencher at the ends thereof. For SNP detection assays it is useful to provide such dye and dye quencher molecules in pairs, e.g. where each molecule has a distinct fluorescent dye at the 5' end and has identical nucleotide sequence except for a single nucleotide polymorphism. It is well known in the art how to design oligonucleotide PCR probe pairs for annealing to a target segment of DNA for the purpose of reporting, wherein the sequence of the target is known such as the polymorphic marker sequences provided in the present invention.

For assays where the isolated nucleic molecule is designed to hybridize adjacent to a polymorphism which is detected by single base extension, such molecules can comprise at least 15, more preferably at least 16 or 17, nucleotide bases in a sequence which is at least 90 percent, preferably at least 95%, identical to a sequence of the same number of consecutive nucleotides in either strand of a segment of polymorphic soybean DNA. In this case, the isolated nucleotide provides for incorporation of a detectable label. This detectable label can be an isotope, a fluorophore, an oxidant, a reductant, a nucleotide or a hapten.

For assays involving use of Flap endonucleases (i.e. INVADER® assays). In certain embodiments, the compositions would comprise at least two isolated nucleic acid molecules for detecting a molecular marker representing a polymorphism in soybean DNA, wherein a first nucleic acid molecule of the composition comprises an oligonucleotide that includes the polymorphic nucleotide residue and at least 8 nucleotides that are immediately adjacent to a 3' end of said polymorphic nucleotide residue, wherein a second nucleic acid molecule of the composition comprises an oligonucleotide that includes the polymorphic nucleotide residue and at least 8 nucleotides that are immediately adjacent to a 5' end of said polymorphic nucleotide residue, and wherein the polymorphism is identified in Table 1 or Table 3. In certain embodiments, isolated nucleic acid molecule compositions suitable for typing the polymorphisms of Table 1 or Table 3 with the Flap endonuclease would comprise at least one primary probe with a "universal" 5' Flap sequence, at least one secondary or "INVADER®" probe, and at least one "FRET" cassettes containing the labelled base and quencher base that contains sequences complementary to the "universal Flap sequence" that is released from the primary probe upon cleavage.

Identifying Polymorphisms

SNPs are the result of sequence variation and new polymorphisms can be detected by sequencing random genomic or cDNA molecules. In one aspect, polymorphisms in a genome can be determined by comparing cDNA sequence from different lines. While the detection of polymorphisms by comparing cDNA sequence is relatively convenient, evaluation of cDNA sequence allows no information about the position of introns in the corresponding genomic DNA. Moreover, polymorphisms in non-coding sequence cannot be identified from cDNA. This can be a disadvantage, e.g. when using cDNA-derived polymorphisms as markers for genotyping of genomic DNA. More efficient genotyping assays can be designed if the scope of polymorphisms includes those present in non-coding unique sequence.

Genomic DNA sequence is more useful than cDNA for identifying and detecting polymorphisms. Polymorphisms in a genome can be determined by comparing genomic DNA sequence from different lines. However, the genomic DNA of higher eukaryotes typically contain a large fraction of repetitive sequence and transposons. Genomic DNA can be more efficiently sequenced if the coding/unique fraction is enriched by subtracting or eliminating the repetitive sequence.

There are a number of strategies well known in the art that can be employed to enrich for coding/unique sequence. Examples of these include the use of enzymes which are sensitive to cytosine methylation, the use of the McrBC endonuclease to cleave repetitive sequence, and the printing of microarrays of genomic libraries which are then hybridized with repetitive sequence probes.

In a preferred embodiment, coding DNA is enriched by exploiting differences in methylation pattern; the DNA of higher eukaryotes tends to be very heavily methylated, however it is not uniformly methylated. In fact, repetitive sequence is much more highly methylated than coding sequence. See U.S. Pat. No. 6,017,704 for methods of mapping and assessment of DNA methylation patterns in CG islands. Briefly, some restriction endonucleases are sensitive to the presence of methylated cytosine residues in their recognition site. Such methylation sensitive restriction endonucleases may not cleave at their recognition site if the cytosine residue in either an overlapping 5'-CG-3' or an overlapping 5'-CNG-3' is methylated. In order to enrich for coding/unique sequence soybean libraries can be constructed from genomic DNA digested with Pst I (or other methylation sensitive enzymes), and size fractionated by agarose gel electrophoresis.

One method for reducing repetitive DNA comprises the construction of reduced representation libraries by separating repetitive sequence from fragments of genomic DNA of at least two varieties of a species, fractionating the separated genomic DNA fragments based on size of nucleotide sequence and comparing the sequence of fragments in a fraction to determine polymorphisms. More particularly, these methods of identifying polymorphisms in genomic DNA comprises digesting total genomic DNA from at least two variants of a eukaryotic species with a methylation sensitive endonuclease to provide a pool of digested DNA fragments. The average nucleotide length of fragments is smaller for DNA regions characterized by a lower percent of 5-methylated cytosine. Such fragments are separable, e.g. by gel electrophoresis, based on nucleotide length. A fraction of DNA with less than average nucleotide length is separated from the pool of digested DNA. Sequences of the DNA in a fraction are compared to identify polymorphisms. As compared to coding sequence, repetitive sequence is more likely to comprise 5-methylated cytosine, e.g. in -CG- and -CNG- sequence segments. In one embodiment of the method, genomic DNA from at least two different inbred varieties of a crop plant is digested with a with a methylation sensitive endonuclease selected from the group consisting of Aci I, Apa I, Age I, Bsr F I, BssH II, Eag I, Eae I, Hha I, HinP1 I, Hpa II, Msp I, MspM II, Nar I, Not I, Pst I, Pvu I, Sac II, Sma I, Stu I and Xho I to provide a pool of digested DNA which is physically separated, e.g. by gel electrophoresis. Comparable size fractions of DNA are obtained from digested DNA of each of said varieties. DNA molecules from the comparable fractions are inserted into vectors to construct reduced representation libraries of genomic DNA clones which are sequenced and compared to identify polymorphisms.

An alternative method for enriching coding region DNA sequence enrichment uses McrBC endonuclease restriction, which cleaves methylated cytosine-containing DNA. Reduced representation libraries can be constructed using genomic DNA fragments which are cleaved by physical shearing or digestion with any restriction enzyme.

A further method to enrich for coding/unique sequence consists of construction of reduced representation libraries (using methylation sensitive or non-methylation sensitive enzymes), printing microarrays of the library on nylon membrane, followed by hybridization with probes made from repetitive elements known to be present in the library. The repetitive sequence elements are identified, and the library is re-arrayed by picking only the negative clones. Such methods provide segments of reduced representation genomic DNA from a plant which has genomic DNA comprising regions of DNA with relatively higher levels of methylated cytosine and regions of DNA with relatively lower levels of methylated cytosine. The reduced representation segments of this invention comprise genomic DNA from a region of DNA with relatively lower levels of methylated cytosine and are provided in fractions characterized by nucleotide size of said segments, e.g. in the range of 500 to 3000 bp.

Typing Polymorphisms in Soybean Genomic DNA Samples

Polymorphisms in DNA sequences can be detected or typed by a variety of effective methods well known in the art including, but not limited to, those disclosed in U.S. Pat. Nos. 5,468,613 and 5,217,863; 5,210,015; 5,876,930; 6,030,787; 6,004,744; 6,013,431; 5,595,890; 5,762,876; 5,945,283; 5,468,613; 6,090,558; 5,800,944; and 5,616,464, all of which are incorporated herein by reference in their entireties. However, the compositions and methods of this invention can be used in conjunction with any polymorphism typing method to type polymorphisms in soybean genomic DNA samples. These soybean genomic DNA samples used include but are not limited to soybean genomic DNA isolated directly from a soybean plant, cloned soybean genomic DNA, or amplified soybean genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Genome Res. 13:513-523 (2003); Cui et al., Bioinformatics 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening a plurality of polymorphisms. A single-feature polymorphism (SFP) is a polymorphism detected by a single probe in an oligonucleotide array, wherein a feature is a probe in the array. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616,464 employing at least one pair of probes having sequences homologous to adjacent portions of the target nucleic acid sequence and having side chains which non-covalently bind to form a stem upon base pairing of said probes to said target nucleic acid sequence. At least one of the side chains has a photoactivatable group which can form a covalent cross-link with the other side chain member of the stem.

Other methods for detecting SNPs and Indels include single base extension (SBE) methods. Examples of SBE methods include, but are not limited to, those disclosed in U.S. Pat. Nos. 6,004,744; 6,013,431; 5,595,890; 5,762,876; and 5,945,283. SBE methods are based on extension of a nucleotide primer that is immediately adjacent to a polymorphism to incorporate a detectable nucleotide residue upon extension of the primer. In certain embodiments, the SBE method uses three synthetic oligonucleotides. Two of the oligonucleotides serve as PCR primers and are complementary to sequence of the locus of soybean genomic DNA which flanks a region containing the polymorphism to be assayed. Following amplification of the region of the soybean genome containing the polymorphism, the PCR product is mixed with the third oligonucleotide (called an extension primer) which is designed to hybridize to the amplified DNA immediately adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In a preferred method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

A useful assay is available from AB Biosystems as the TAQMAN® assay which employs four synthetic oligonucleotides in a single reaction that concurrently amplifies the soybean genomic DNA, discriminates between the alleles present, and directly provides a signal for discrimination and detection. Two of the four oligonucleotides serve as PCR primers and generate a PCR product encompassing the polymorphism to be detected. Two others are allele-specific fluorescence-resonance-energy-transfer (FRET) probes. In the assay, two FRET probes bearing different fluorescent reporter dyes are used, where a unique dye is incorporated into an oligonucleotide that can anneal with high specificity to only one of the two alleles. Useful reporter dyes include, but are not limited to, 6-carboxy-4,7,2',T-tetrachlorofluorecein (TET), 2'-chloro-7'-phenyl-1,4-dichloro-6-carboxyfluorescein (VIC) and 6-carboxyfluorescein phosphoramidite (FAM). A useful quencher is 6-carboxy-N,N,N',N'-tetramethylrhodamine (TAMRA). Additionally, the 3'end of each FRET probe is chemically blocked so that it can not act as a PCR primer. Also present is a third fluorophore used as a passive reference, e.g., rhodamine X (ROX) to aid in later normalization of the relevant fluorescence values (correcting for volumetric errors in reaction assembly). Amplification of the genomic DNA is initiated. During each cycle of the PCR, the FRET probes anneal in an allele-specific manner to the template DNA molecules. Annealed (but not non-annealed) FRET probes are degraded by TAQ DNA polymerase as the enzyme encounters the 5' end of the annealed probe, thus releasing the fluorophore from proximity to its quencher. Following the PCR, the fluorescence of each of the two fluorescers, as well as that of the passive reference, is determined fluorometrically. The normalized intensity of fluorescence for each of the two dyes will be proportional to the amounts of each allele initially present in the sample, and thus the genotype of the sample can be inferred.

To design primers and probes for the assay the locus sequence is first masked to prevent design of any of the three primers to sites that match known soybean repetitive elements (e.g., transposons) or are of very low sequence complexity (di- or tri-nucleotide repeat sequences). Design of primers to such repetitive elements will result in assays of low specificity, through amplification of multiple loci or annealing of the FRET probes to multiple sites.

PCR primers are designed (a) to have a length in the size range of 15 to 25 bases and matching sequences in the polymorphic locus, (b) to have a calculated melting temperature in the range of 57 to 60° C., e.g. corresponding to an optimal PCR annealing temperature of 52 to 55° C., (c) to produce a product which includes the polymorphic site and typically has a length in the size range of 75 to 250 base pairs. However, PCR techniques that permit amplification of fragments of up to 1000 base pairs or more in length have also been disclosed in U.S. Pat. No. 6,410,277. The PCR primers are preferably located on the locus so that the polymorphic site is at least one base away from the 3' end of each PCR primer. However, it is understood that the PCR primers can be up to 1000 base pairs or more away from the polymorphism and still provide for amplification of a corresponding DNA fragment of 1000 base pairs or more that contains the polymorphism and can be used in typing assays. The PCR primers must not contain regions that are extensively self- or inter-complementary.

FRET probes are designed to span the sequence of the polymorphic site, preferably with the polymorphism located in the 3' most ⅔ of the oligonucleotide. In the preferred embodiment, the FRET probes will have incorporated at their 3' end a chemical moiety which, when the probe is annealed to the template DNA, binds to the minor groove of the DNA, thus enhancing the stability of the probe-template complex. The probes should have a length in the range of 12 to 17 bases, and with the 3'MGB, have a calculated melting temperature of 5 to 7° C. above that of the PCR primers. Probe design is disclosed in U.S. Pat. Nos. 5,538,848, 6,084,102, and 6,127,121.

Oligonucleotide probes for typing single nucleotide polymorphisms through use of Flap Endonuclease-mediated (IN-VADER®, Third Wave Technologies, Madison Wis.) assays are also contemplated. In these assays, a flap endonuclease (cleavase) cuts a triple-helix created by hybridization of two overlapping oligonucleotides to the sequence that is typed (Lyamichev et al., Nat. Biotechnol., 17: 292-296, 1999). The sequence that is typed can be either soybean genomic DNA, cloned soybean genomic DNA or amplified soybean genomic DNA. Cleavage of one of the oligonucleotides that hybridizes to the sequence to be typed releases a flap that in turn forms a triple helix with a "FRET Cassette" oligonucleotide, resulting in a secondary cleavage reaction that releases a fluorescence resonance energy transfer (FRET) label. Embodiments where a single allele of a polymorphism is typed using a single FRET label have been described (Mein C. A., et al. Genome Res., 10: 330-343, 2000). In other embodiments of this method, two alleles of a polymorphism can be simultaneously typed by using different FRET labels. (Lyamichev et al., Ibid). High-throughput Flap Endonuclease-mediated assays have also been described that are suitable for creating sets of nucleotides for typing multiple polymorphisms (Olivier, et al., Nucleic Acids Res. 30(12): e53, 2002).

Isolated nucleic acid molecule compositions suitable for typing the polymorphisms of Table 1 or Table 3 with the cleavase can comprise at least one primary probe with a "universal" 5' flap sequence, at least one secondary or "INVADER®" probe, and at least one "FRET" cassettes containing the labelled base and quencher base that contains sequences complementary to the "universal flap sequence" that is released from the primary probe upon cleavage. When the typed sequence is amplified soybean genomic DNA, flanking PCR primers similar to those described in the preceding paragraphs can also be used. The design of such probes requires only the provision of about 40 to 50 nucleotides on either side of the polymorphic base noted in Table 1 or Table 3. General aspects of designing probes for Flap endonuclease assays are described in "Single Nucleotide Polymorphisms" (Methods and Protocols) Volume 212, Chapter 16, V. Lyamichev and B. Neri pp. 229-240 Humana Press. 2002).

Use of Polymorphisms to Establish Marker/Trait Associations

The polymorphisms in the loci of this invention can be used in the identification of marker/trait associations which are inferred from statistical analysis of genotypes and phenotypes of the members of a population. These members may be individual organisms, e.g. soybean, families of closely related individuals, inbred lines, doubled haploids or other groups of closely related individuals. Such soybean groups are referred to as "lines", indicating line of descent. The population may be descended from a single cross between two individuals or two lines (e.g. a mapping population) or it may consist of individuals with many lines of descent. Each individual or line is characterized by a single or average trait phenotype and by the genotypes at one or more marker loci.

Several types of statistical analysis can be used to infer marker/trait association from the phenotype/genotype data, but a basic idea is to detect molecular markers, i.e. polymorphisms, for which alternative genotypes have significantly different average phenotypes. For example, if a given marker locus A has three alternative genotypes (AA, Aa and aa), and if those three classes of individuals have significantly different phenotypes, then one infers that locus A is associated with the trait. The significance of differences in phenotype may be tested by several types of standard statistical tests such as linear regression of molecular marker genotypes on phenotype or analysis of variance (ANOVA). Commercially available, statistical software packages commonly used to do this type of analysis include SAS Enterprise Miner (SAS Institute Inc., Cary, N.C.) and Splus (Insightful Corporation. Cambridge, Mass.). When many molecular markers are tested simultaneously, an adjustment such as Bonferonni correction is made in the level of significance required to declare an association.

For the purpose of QTL mapping, the markers included should be diagnostic of origin in order for inferences to be made about subsequent populations. Molecular markers based on SNPs are ideal for mapping because the likelihood that a particular SNP allele is derived from independent origins in the extant populations of a particular species is very low. As such, SNP molecular markers are useful for tracking and assisting introgression of QTLs, particularly in the case of haplotypes.

Often the goal of an association study is not simply to detect marker/trait associations, but to estimate the location of genes affecting the trait directly (i.e. QTLs) relative to the marker locations. In a simple approach to this goal, one makes a comparison among marker loci of the magnitude of difference among alternative genotypes or the level of significance of that difference. Trait genes are inferred to be located nearest the marker(s) that have the greatest associated genotypic difference. The genetic linkage of additional marker molecules can be established by a gene mapping model such as, without limitation, the flanking marker model reported by Lander et al. (Lander et al. 1989 Genetics, 121:185-199), and the interval mapping, based on maximum likelihood methods described therein, and implemented in the software package MAPMAKER/QTL (Lincoln and Lander, *Mapping Genes Controlling Quantitative Traits Using MAPMAKER/QTL*, Whitehead Institute for Biomedical Research, Massachusetts, (1990). Additional software includes Qgene, Version 2.23 (1996), Department of Plant Breeding and Biometry, 266 Emerson Hall, Cornell University, Ithaca, N.Y.). Use of Qgene software is a particularly preferred approach.

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL). The LOD score essentially indicates how much more likely the data are to have arisen assuming the presence of a QTL versus in its absence. The LOD threshold value for avoiding a false positive with a given confidence, say 95%, depends on the number of markers and the length of the genome. Graphs indicating LOD thresholds are set forth in Lander et al. (1989), and further described by Arús and Moreno-González, *Plant Breeding*, Hayward, Bosemark, Romagosa (eds.) Chapman & Hall, London, pp. 314-331 (1993).

Additional models can be used. Many modifications and alternative approaches to interval mapping have been reported, including the use of non-parametric methods (Kruglyak et al. 1995 Genetics, 139:1421-1428). Multiple regression methods or models can be also used, in which the trait is regressed on a large number of markers (Jansen, *Biometrics in Plant Breed*, van Oijen, Jansen (eds.) Proceedings of the Ninth Meeting of the Eucarpia Section Biometrics in Plant Breeding, The Netherlands, pp. 116-124 (1994); Weber and Wricke, *Advances in Plant Breeding*, Blackwell, Berlin, 16 (1994)). Procedures combining interval mapping with regression analysis, whereby the phenotype is regressed onto a single putative QTL at a given marker interval, and at the same time onto a number of markers that serve as 'cofactors,' have been reported by Jansen et al. (Jansen et al. 1994 Genetics, 136:1447-1455) and Zeng (Zeng 1994 Genetics 136:1457-1468). Generally, the use of cofactors reduces the bias and sampling error of the estimated QTL positions (Utz and Melchinger, *Biometrics in Plant Breeding*, van Oijen, Jansen (eds.) Proceedings of the Ninth Meeting of the Eucarpia Section Biometrics in Plant Breeding, The Netherlands, pp. 195-204 (1994), thereby improving the precision and efficiency of QTL mapping (Zeng 1994). These models can be extended to multi-environment experiments to analyze genotype-environment interactions (Jansen et al. 1995 Theor. Appl. Genet. 91:33-3).

An alternative to traditional QTL mapping involves achieving higher resolution by mapping haplotypes, versus individual markers (Fan et al. 2006 Genetics 172:663-686) as one of the limitations of traditional QTL mapping research has been the fact that inferences are restricted to the particular parents of the mapping population and the genes or gene combinations of these parental varieties. This approach tracks blocks of DNA known as haplotypes, as defined by polymorphic markers, which are assumed to be identical by descent in the mapping population. It has long been recognized that genes and genomic sequences may be identical by state (i.e., identical by independent origins) or identical by descent (i.e., through historical inheritance from a common progenitor) which has tremendous bearing on studies of linkage disequilibrium and, ultimately, mapping studies (Nordberg et al. 2002 Trends Gen.). Historically, genetic markers were not appropriate for distinguishing identical in state or by descent. However, newer classes of markers, such as SNPs (single nucleotide polymorphisms), are more diagnostic of origin. The likelihood that a particular SNP allele is derived from independent origins in the extant populations of a particular species is very low. Polymorphisms occurring in linked genes are randomly assorted at a slow, but predictable rate, described by the decay of linkage disequilibrium or, alternatively, the approach of linkage equilibrium. Consequences of this well-established scientific discovery are that long stretches of coding DNA, defined by a specific combination of polymorphisms, are very unique and extremely improbable of existing in duplication except through linkage disequilibrium, which is indicative of recent co-ancestry from a common progenitor. The probability that a particular genomic region, as defined by some combination of alleles, indicates absolute identity of the entire intervening genetic sequence is dependent on the number of linked polymorphisms in this genomic region, barring the occurrence of recent mutations in the interval. Herein, such genomic regions are referred to as haplotype windows. Each haplotype within that window is defined by specific combinations of alleles; the greater the number of alleles, the greater the number of potential haplotypes, and the greater the certainty that identity by state is a result of identity by descent at that region. During the development of new lines, ancestral haplotypes are maintained through the process and are typically thought of as 'linkage blocks' that are inherited as a unit through a pedigree. Further, if a specific haplotype has a known effect, or phenotype, it is possible to extrapolate its effect in other lines with the same haplotype, as determined using one or more diagnostic markers for that haplotype window.

This assumption results in a larger effective sample size, offering greater resolution of QTL. Methods for determining the statistical significance of a correlation between a phenotype and a genotype, in this case a haplotype, may be determined by any statistical test known in the art and with any accepted threshold of statistical significance being required. The application of particular methods and thresholds of significance are well with in the skill of the ordinary practitioner of the art.

Construction of Genetic Maps

In another aspect of the invention the polymorphism in the loci of the invention are mapped onto the soybean genome, e.g. as a genetic map of the soybean genome comprising map positions of two or more polymorphisms, as indicated in Table 1, more preferably as indicated in Table 3. Such a genetic map is illustrated in FIG. 1. The genetic map data can also be recorded on computer readable medium. Preferred embodiments of the invention provide genetic maps of polymorphisms at high densities, e.g. at least 150 or more, say at least 500 or 1000, polymorphisms across a map of the soybean genome. Especially useful genetic maps comprise polymorphisms at an average distance of not more than 10 centi-Morgans (cM) on a linkage group.

Linkage Disequilibrium Mapping and Association Studies

Another approach to determining trait gene location is to analyze marker/trait associations in a population within which individuals differ at both trait and marker loci. Certain marker alleles may be associated with certain trait locus alleles in this population due to population genetic process such as the unique origin of mutations, founder events, random drift and population structure. This association is referred to as linkage disequilibrium.

In plant breeding populations, linkage disequilibrium (LD) is the level of departure from random association between two or more loci in a population and LD often persists over large chromosomal segments. Although it is possible for one to be concerned with the individual effect of each gene in the segment, for a practical plant breeding purpose the emphasis is typically on the average impact the region has for the trait(s) of interest when present in a line, hybrid or variety. In linkage disequilibrium mapping, one compares the trait values of individuals with different genotypes at a marker locus. Typically, a significant trait difference indicates close proximity between marker locus and one or more trait loci. If the marker density is appropriately high and the linkage disequilibrium occurs only between very closely linked sites on a chromosome, the location of trait loci can be very precise.

Marker-Assisted Breeding and Marker-Assisted Selection

When a quantitative trait locus (QTL) has been localized in the vicinity of molecular markers, those markers can be used to select for improved values of the trait without the need for phenotypic analysis at each cycle of selection. In marker-assisted breeding and marker-assisted selection, associations between QTL and markers are established initially through genetic mapping analysis (as in A.1 or A.2). In the same process, one determines which molecular marker alleles are linked to favorable QTL alleles. Subsequently, marker alleles associated with favorable QTL alleles are selected in the population. This procedure will improve the value of the trait provided that there is sufficiently close linkage between markers and QTLs. The degree of linkage required depends upon the number of generations of selection because, at each generation, there is opportunity for breakdown of the association through recombination.

The associations between specific marker alleles and favorable QTL alleles also can be used to predict what types of progeny may segregate from a given cross. This prediction may allow selection of appropriate parents to generation populations from which new combinations of favorable QTL alleles are assembled to produce a new inbred line. For example, if line A has marker alleles previously known to be associated with favorable QTL alleles at loci 1, 20 and 31, while line B has marker alleles associated with favorable effects at loci 15, 27 and 29, then a new line could be developed by crossing A×B and selecting progeny that have favorable alleles at all 6 QTL.

Molecular markers are used to accelerate introgression of transgenes into new genetic backgrounds (i.e. into a diverse range of germplasm). Simple introgression involves crossing a transgenic line to an elite inbred line and then backcrossing the hybrid repeatedly to the elite (recurrent) parent, while selecting for maintenance of the transgene. Over multiple backcross generations, the genetic background of the original transgenic line is replaced gradually by the genetic background of the elite inbred through recombination and segregation. This process can be accelerated by selection on molecular marker alleles that derive from the recurrent parent.

Further, a fingerprint of an inbred line is the combination of alleles at a set of two or more marker loci. High density fingerprints can be used to establish and trace the identity of germplasm, which has utility in establishing a database of marker-trait associations to benefit an overall crop breeding program, as well as germplasm ownership protection.

Methods for Selecting Parent, Progeny, or Tester Plants for Plant Breeding

It is also contemplated that the polymorphism provided herein can be used to select a parent, progeny, or tester plants for plant breeding. The ability to select such plants from populations of plants that are otherwise phenotypically indistinguishable can accelerate plant breeding and reduce costs incurred by performing phenotypic trait analyses. The methods of selecting plants for breeding comprise the steps of a) determining associations between a plurality of polymorphisms identified in Table 1 or Table 3 and a plurality of traits in at least a first and a second inbred line of soybean; b) determining an allelic state of one or a plurality of polymorphism in a parent, progeny or tester plant; and c) selecting the parent, progeny or tester that has a more favorable combination of associated traits. In certain applications, the parent, progeny or tester plant selected by this method is an inbred soybean line. In other embodiments, the favorable combination of associated traits provides for improved heterosis.

In one embodiment, determining the genotype of at least two polymorphisms will assist in the selection of parents for use in breeding crosses. This determination confers an advantage to the breeder for the creation of crosses wherein at least two preferred genomic regions are targeted in order to generate progeny with the at least two preferred genomic regions. In another aspect, the determination of the genotype for at least two polymorphisms can provide the basis for selection decisions among progeny wherein those progeny comprising preferred genomic regions are advanced in a breeding program. In yet another aspect, tester lines, which are used to evaluate the combining ability of inbreds in hybrid combinations, can be chosen for inclusion in an inbred testing scheme based on the presence, or absence, of at least two genomic regions in order to ensure crosses are made between distinct germplasm pools, i.e., different heterotic groups.

Hybrid Prediction

Commercial soybean seed is produced by making hybrids between two elite inbred lines that belong to different "heterotic groups". These groups are sufficiently distinct genetically that hybrids between them show high levels of heterosis or hybrid vigor (i.e. increased performance relative to the parental lines). By analyzing the marker constitution of good hybrids, one can identify sets of alleles at different loci in both male and female lines that combine well to produce heterosis. Understanding these patterns, and knowing the marker constitution of different inbred lines, can allow prediction of the level of heterosis between different pairs of lines. These predictions can narrow down the possibilities of which line(s) of opposite heterotic group should be used to test the performance of a new inbred line.

This invention provides methods for improving heterosis in hybrid soybean. In such methods associations are developed between a plurality of polymorphisms which are linked to polymorphic loci of the invention and traits in more than two inbred lines of soybean. Two of such inbred lines having complementary heterotic groups which are predicted to improve heterosis are selected for breeding. The methods for improving heterosis comprise the steps of: (a) determining associations between a plurality of polymorphisms identified in Table 1 or Table 3 and a plurality of traits in more than two inbred lines of soybean; (b) assigning two inbred lines selected from the inbred lines of step (a) to heterotic groups, (c) making at least one cross between at least two inbred lines from step (b), wherein each inbred line comes from a distinct and complementary heterotic group and wherein the complementary heterotic groups are optimized for genetic features that improve heterosis; and (d) obtaining a hybrid progeny plant from said cross in step (c), wherein said hybrid progeny plant displays increased heterosis relative to progeny derived from a cross with an unselected inbred line. These methods can also comprise traditional single crosses (i.e., between a two inbred lines, ideally from different heterotic groups), three-way crosses (a single cross is followed by a cross to a third inbred line), and double crosses (also known as a four-way cross, this is crossing the progeny of two single crosses) in step (c). Crosses can be effected by making manual crosses between selected male-fertile parents or by using male sterility systems. Development and selection of elite inbred lines, the crossing of these lines and selection of superior hybrid crosses to identify new elite soybean hybrids is described in Bernardo, Breeding for Quantitative Traits in Plants, Stemma Press, Woodbury, Minn., 2002.

Identity by Descent

One theory of heterosis predicts that regions of identity by descent (IBD) between the male and female lines used to produce a hybrid will reduce hybrid performance. Identity by descent can be inferred from patterns of marker alleles in different lines. An identical string of markers at a series of adjacent loci may be considered identical by descent if it is unlikely to occur independently by chance. Analysis of marker fingerprints in male and female lines can identify regions of IBD. Knowledge of these regions can inform the choice of hybrid parents, since avoiding IBD in hybrids is likely to improve performance. This knowledge may also inform breeding programs in that crosses could be designed to produce pairs of inbred lines (one male and one female) that show little or no IBD.

Libraries of Nucleic Acid Molecules for Use in Genotyping

Libraries of nucleic acids provided by this invention can be used in activities related to soybean germplasm improvement, including but not limited to using the plant for making breeding crosses, further genetic or phenotypic testing of the plant, advancement of the plant through self fertilization, use of the plant or parts thereof for transformation, and use of the plant or parts thereof for mutagenesis. The distinct sets of nucleic acids in the libraries can be sampled, accessed, or individually queried for any set or subset or combination thereof to type any of the soybean genomic DNA provided herein in Tables 1 or 3. In general, the libraries comprising at least two distinct sets of nucleic acid molecules wherein each of said distinct sets of nucleic acid molecules permits typing of a corresponding soybean genomic DNA polymorphism identified in Table 1 or Table 3.

In one embodiment, the distinct sets of nucleic acid molecules that permits typing of a corresponding soybean genomic DNA polymorphism identified in Table 1 or Table 3 are distributed in individual wells of a microtiter plate. In certain embodiments, each well of the microtiter plate will contain one or more nucleic acid molecules that permit typing of just one soybean polymorphism identified in Table 1 or Table 3. However, other embodiments where each well of the microtiter plate contains one or more nucleic acid molecules that permit typing of more than one soybean polymorphism identified in Table 1 or Table 3 are also contemplated. The microtiter plates can have as few as 8 wells, or as many as 24, 96, 384, 1536 or 3456 wells. The microtiter plates can be constructed from materials including, but not limited to, polystyrene, polypropylene, or cyclo-olefin plastics. The nucleic acid molecules in each well can be either in solution or in a dry (i.e. lyophilized form). In general, the nucleic acids will be distributed to the wells of the microtiter plate such that the nucleic acids in each well of the microtiter plate are known. However, in other embodiments where the nucleic cid molecules are associated with a unique identifier (such as a unique dye or other unique identifying label), the nucleic acids can be randomly distributed into the wells of the microtiter plate. As is clear from this description, libraries comprising nucleic acids immobilized on solid supports (such as beads) that are distributed in wells of microtiter plates are also contemplated.

In other embodiments, the nucleic acids that permit typing of a soybean genomic polymorphism identified in Table 1 or Table 3 are immobilized (i.e. covalently linked) to a solid support. Solid supports include, but are not limited to, beads, chips, arrays, or filters.

The beads used as a solid support can be magnetic beads to facilitate purification of hybridization complexes. Alternatively, the beads can contain a unique identifying label. In particular, beads dyed with fluorochromes that can be distinguished by their spectrophotometric or fluorometric properties can be coupled to the nucleic acid molecules for typing polymorphisms. Such bead based systems for typing polymorphisms have been described (U.S. Pat. No. 5,736,330). Dye labelled beads, analysis reagents and apparati for typing polymorphisms have also been described (U.S. Pat. Nos. 6,649,414, 6,599,331, and 6,592,822) and are available from Luminex Corporation (Austin, Tex., USA). As noted above, the bead-linked nucleic acid molecules of the library can also be.

The chips, arrays, or filters can also be used to immobilize the nucleic acid molecules for typing of the polymorphisms of Tables 1 or Table 3. In certain embodiments, the nucleic acid markers for typing a given polymorphism will be immobilized at a defined physical location on the array such that typing data from that location that corresponds to a given polymorphism can be generated and recorded for subsequent analysis. Methods of making and using arrays for typing of polymorphisms include, but are not limited to, those described in U.S. Pat. No. 5,858,659 (for hybridization based methods) and U.S. Pat. No. 6,294,336 (for single base extension methods).

Use of Polymorphism Assays for Mapping a Library of DNA clones

The polymorphisms and loci represented by the molecular markers of this invention are useful for identifying and mapping DNA sequence of QTLs and genes linked to the molecular markers. For instance, BAC or YAC clone libraries can be queried using molecular markers linked to a trait to find a clone containing specific QTLs and genes associated with the trait. For instance, QTLs and genes in a plurality, e.g. hundreds or thousands, of large, multi-gene sequences can be identified by hybridization with an oligonucleotide probe which hybridizes to a mapped and/or linked molecular marker, wherein one or more molecular markers can be assayed. Such hybridization screening can be improved by providing clone sequence in a high density array. The screening method is more preferably enhanced by employing a pooling strategy to significantly reduce the number of hybridizations required to identify a clone containing the molecular marker. When the molecular markers are mapped, the screening effectively maps the clones.

For instance, in a case where thousands of clones are arranged in a defined array, e.g. in 96 well plates, the plates can be arbitrarily arranged in three-dimensionally, arrayed stacks of wells each comprising a unique DNA clone. The wells in each stack can be represented as discrete elements in a three dimensional array of rows, columns and plates. In one aspect of the invention the number of stacks and plates in a stack are about equal to minimize the number of assays. The stacks of plates allow the construction of pools of cloned DNA.

For a three-dimensionally arrayed stack pools of cloned DNA can be created for (a) all of the elements in each row, (b) all of the elements of each column, and (c) all of the elements of each plate. Hybridization screening of the pools with an oligonucleotide probe which hybridizes to a molecular marker unique to one of the clones will provide a positive indication for one column pool, one row pool and one plate pool, thereby indicating the well element containing the target clone.

In the case of multiple stacks, additional pools of all of the clone DNA in each stack allows indication of the stack having the row-column-plate coordinates of the target clone. For instance, a 4608 clone set can be disposed in 48 96-well plates. The 48 plates can be arranged in 8 sets of 6 plate stacks providing 6×12×8 three-dimensional arrays of elements, i.e. each stack comprises 6 stacks of 8 rows and 12 columns. For the entire clone set there are 36 pools, i.e. 6 stack pools, 8 row pools, 12 column pools and 8 stack pools. Thus, a maximum of 36 hybridization reactions is required to find the clone harboring QTLs or genes associated or linked to each mapped molecular marker.

Once a clone is identified, oligonucleotide primers designed from the locus of the molecular marker can be used for positional cloning of the linked QTL and/or genes.

Computer Readable Media and Databases

The sequences of nucleic acid molecules of this invention can be "provided" in a variety of mediums to facilitate use, e.g. a database or computer readable medium, which can also contain descriptive annotations in a form that allows a skilled artisan to examine or query the sequences and obtain useful information. In one embodiment of the invention computer readable media may be prepared that comprise nucleic acid sequences where at least 10% or more, e.g. at least 25%, or even at least 50% or more of the sequences of the loci and nucleic acid molecules representing the molecular markers of this invention. For instance, such database or computer readable medium may comprise sets of the loci of this invention or sets of primers and probes useful for assaying the molecular markers of this invention. In addition such database or computer readable medium may comprise a figure or table of the mapped or unmapped molecular markers or this invention and genetic maps.

As used herein "database" refers to any representation of retrievable collected data including computer files such as text files, database files, spreadsheet files and image files, printed tabulations and graphical representations and combinations of digital and image data collections. In a preferred aspect of the invention, "database" refers to a memory system that can store computer searchable information. Currently, preferred database applications include those provided by DB2, Sybase and Oracle.

As used herein, "computer readable media" refers to any medium that can be read and accessed directly by a computer. Such media include, but are not limited to: magnetic storage media, such as floppy discs, hard disc, storage medium and magnetic tape; optical storage media such as CD-ROM; electrical storage media such as RAM, DRAM, SRAM, SDRAM, ROM, and PROMs (EPROM, EEPROM, Flash EPROM), and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention.

As used herein, "recorded" refers to the result of a process for storing information in a retrievable database or computer readable medium. For instance, a skilled artisan can readily adopt any of the presently known methods for recording information on computer readable medium to generate media comprising the mapped polymorphisms and other nucleotide sequence information of the present invention. A variety of data storage structures are available to a skilled artisan for creating a computer readable medium where the choice of the data storage structure will generally be based on the means chosen to access the stored information. In addition, a variety of data processor programs and formats can be used to store the polymorphisms and nucleotide sequence information of the present invention on computer readable medium.

Computer software is publicly available which allows a skilled artisan to access sequence information provided in a computer readable medium. The examples which follow demonstrate how software which implements a search algorithm such as the BLAST algorithm (Altschul et al., J. Mol. Biol. 215:403-410 (1990), incorporated herein by reference) and the BLAZE algorithm (Brutlag et al., Comp. Chem. 17:203-207 (1993), incorporated herein by reference) on a Sybase system can be used to identify DNA sequence which is homologous to the sequence of loci of this invention with a high level of identity. Sequence of high identity can be compared to find polymorphic markers useful with soybean varieties.

The present invention further provides systems, particularly computer-based systems, which contain the sequence information described herein. Such systems are designed to identify commercially important sequence segments of the nucleic acid molecules of this invention. As used herein, "a computer-based system" refers to the hardware, software and memory used to analyze the nucleotide sequence information. A skilled artisan can readily appreciate that any one of the currently available computer-based system are suitable for use in the present invention.

As indicated above, the computer-based systems of the present invention comprise a database having stored therein polymorphic markers, genetic maps, and/or the sequence of nucleic acid molecules of the present invention and the necessary hardware and software for supporting and implementing genotyping applications. Such computer-based systems can be used to read, sort or analyze soybean genotypic data. Key components of the computer-based system include: a) a data storage device comprising a computer readable medium wherein at least two soybean genomic DNA polymorphisms identified in Table 1 or Table 3 are recorded thereon; b) a search device for comparing a soybean genomic DNA sequence from at least one test soybean plant to the polymorphism sequences of the data storage device of step (a) to identify homologous or non-homologous sequences; and, c) a retrieval device for identifying the homologous or non-homologous sequences(s) of the test soybean genomic sequences of step (b). Computer based methods and systems (e.g. apparati) for conducting DNA database queries are described in U.S. Pat. No. 6,691,109

In a useful aspect of the invention a data set of polymorphic soybean loci from Table 1 or Table 3 is recorded on a computer readable medium. In one aspect of the invention the soybean genomic polymorphisms are provided in one or more data sets of DNA sequences, i.e. data sets comprising up to a finite number of distinct sequences of polymorphic loci that are recorded on the computer readable media. The finite number of polymorphic loci in a recorded data set can be as few as 2 or up to 1000 or more, e.g. 5, 8, 10, 25, 40, 75, 96, 100, 384 or 500 of the soybean genomic polymorphisms of Table 1 or Table 3. Such data sets are useful for genotyping applications where 1) multiple polymorphisms that identify polymorphisms that are distributed across the genome of soybean are queried; 2) multiple polymorphisms that cluster within an interval are queried; and/or when multiple polymorphisms are queried in large numbers of plants. The data sets recorded on the computer readable media can also comprise corresponding genetic map positions for each of the soybean genomic DNA polymorphisms recorded thereon. In other embodiments, phenotypic trait or phenotypic trait index data is recorded on the computer readable media. In still other embodiments, data associating an allelic state with a parent, progeny, or tester soybean plant is recorded on the computer readable media.

Methods of Breeding

Methods of breeding soybean plants are also contemplated. The methods of breeding soybean plants comprise the steps of: (a) identifying trait values for at least two haplotypes in at least two genomic windows of up to 10 centimorgans for a breeding population of at least two soybean plants; (b) breeding two soybean plants in said breeding population to produce a population of progeny seed; (c) identifying an allelic state of at least one polymorphism identified in Table 1 or Table 3 in each of said windows in said progeny seed to determine the presence of said haplotypes; and (d) selecting progeny seed having a higher trait values identified for determined haplotypes in said progeny seed, thereby breeding a soybean plant. In certain embodiments of these breeding methods, trait values are identified for at least two haplotypes in each adjacent genomic window over essentially the entirety of each chromosome. It is understood that haplotype regions are chromosome segments that persist over multiple generations of breeding and are carried by one or more breeding lines. These segments can be identified with multiple linked marker loci contained in the segments, and the common haplotype identity at these loci in two lines gives a high degree of confidence of the identity by descent of the entire subjacent chromosome segment carried by these lines. Such breeding methods require the use of multiple soybean genomic polymorphisms that are distributed across the soybean genome.

In aspects of this breeding method, trait values are identified for at least two haplotypes in each adjacent genomic window over essentially the entirety of each chromosome. In another useful aspect of the method progeny seed is selected for a higher trait value for yield for a haplotype in a genomic window of up to 10 centimorgans in each chromosome. In another aspect of the invention, the breeding method is directed to increased yield, where the trait value is for the yield trait, where trait values are ranked for haplotypes in each window, and where a progeny seed is selected which has a trait value for yield in a window that is higher than the mean trait value for yield in said window. In certain aspects of the breeding methods the haplotypes are defined using the polymorphisms identified in Table 1 or are defined as being in the set of molecular markers that comprises all of the DNA sequences of SEQ ID NO: 1 through SEQ ID NO:7800, or as being in linkage disequilibrium with one of those polymorphisms.

To facilitate breeding by this method it is useful to compute a value for each trait or a value for a combination of traits, e.g. a multiple trait index. The weight allocated to various traits in a multiple trait index can vary depending on the objectives of breeding. For instance, if yield is a key objective, the yield value may be weighted at 50 to 80%, maturity, lodging, plant height or disease resistance may be weighted at lower percentages in a multiple trait index.

Soybean plants (*Glycine max* L.) can be crossed by either natural or mechanical techniques. Natural pollination occurs in soybeans either by self pollination or natural cross pollination, which typically is aided by pollinating organisms. In either natural or artificial crosses, flowering and flowering time are an important consideration. Soybean is a short-day plant, but there is considerable genetic variation for sensitivity to photoperiod. The critical day length for flowering ranges from about 13 h for genotypes adapted to tropical latitudes to 24 h for photoperiod-insensitive genotypes grown at higher latitudes. Soybeans seem to be insensitive to day length for 9 days after emergence. Photoperiods shorter than the critical day length are required for 7 to 26 days to complete flower induction.

Soybean flowers typically are self-pollinated on the day the corolla opens. The stigma is receptive to pollen about 1 day before anthesis and remains receptive for 2 days after anthesis, if the flower petals are not removed. Filaments of nine stamens are fused, and the one nearest the standard is free. The stamens form a ring below the stigma until about 1 day before anthesis, then their filaments begin to elongate rapidly and elevate the anthers around the stigma. The anthers dehisce on the day of anthesis, pollen grains fall on the stigma, and within 10 h the pollen tubes reach the ovary and fertilization is completed. Self-pollination occurs naturally in soybean with no manipulation of the flowers. For the crossing of two soybean plants, it is typically preferable, although not required, to utilize artificial hybridization. In artificial hybridization, the flower used as a female in a cross is manually cross pollinated prior to maturation of pollen from the flower, thereby preventing self fertilization, or alternatively, the male parts of the flower are emasculated using a technique known in the art. Techniques for emasculating the male parts of a soybean flower include, for example, physical removal of the male parts, use of a genetic factor conferring male sterility, and application of a chemical gametocide to the male parts.

Either with or without emasculation of the female flower, hand pollination can be carried out by removing the stamens and pistil with a forceps from a flower of the male parent and gently brushing the anthers against the stigma of the female flower. Access to the stamens can be achieved by removing the front sepal and keel petals, or piercing the keel with closed forceps and allowing them to open to push the petals away. Brushing the anthers on the stigma causes them to rupture, and the highest percentage of successful crosses is obtained when pollen is clearly visible on the stigma. Pollen shed can be checked by tapping the anthers before brushing the stigma. Several male flowers may have to be used to obtain suitable pollen shed when conditions are unfavorable, or the same male may be used to pollinate several flowers with good pollen shed.

Genetic male sterility is available in soybeans and may be useful to facilitate hybridization in the context of the current invention, particularly for recurrent selection programs. The distance required for complete isolation of a crossing block is not clear; however, out-crossing is less than 0.5% when male-sterile plants are 12 m or more from a foreign pollen source (Boerma and Moradshahi, Crop Sci., 15:858-861, 1975). Plants on the boundaries of a crossing block probably sustain the most out-crossing with foreign pollen and can be eliminated at harvest to minimize contamination.

Once harvested, pods are typically air-dried at not more than 38° C. until the seeds contain 13% moisture or less, then the seeds are removed by hand. Seed can be stored satisfactorily at about 25° C. for up to a year if relative humidity is 50% or less. In humid climates, germination percentage declines rapidly unless the seed is dried to 7% moisture and stored in an air-tight container at room temperature. Long-term storage in any climate is best accomplished by drying seed to 7% moisture and storing it at 10° C. or less in a room maintained at 50% relative humidity or in an air-tight container.

Selected, non-limiting approaches for breeding the plants of the present invention are set forth below. A breeding program can be enhanced using marker assisted selection (MAS) on the progeny of any cross. It is understood that nucleic acid markers of the present invention can be used in a MAS (breeding) program. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability etc. will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred aspect, a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes.

Breeding lines can be tested and compared to appropriate standards in environments representative of the commercial target area(s) for two or more generations. The best lines are candidates for new commercial cultivars; those still deficient in traits may be used as parents to produce new populations for further selection.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Backcross breeding has been used to transfer genes for a simply inherited, highly heritable trait into a desirable homozygous cultivar or inbred line, which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have most attributes of the recurrent parent (e.g., cultivar) and, in addition, the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

The doubled haploid (DH) approach achieves isogenic plants in a shorter time frame. DH plants provide an invaluable tool to plant breeders, particularly for generating inbred lines and quantitative genetics studies. For breeders, DH populations have been particularly useful in QTL mapping, cytoplasmic conversions, and trait introgression. Moreover, there is value in testing and evaluating homozygous lines for plant breeding programs. All of the genetic variance is among progeny in a breeding cross, which improves selection gain.

Most research and breeding applications rely on artificial methods of DH production. The initial step involves the haploidization of the plant which results in the production of a population comprising haploid seed. Non-homozygous lines are crossed with an inducer parent, resulting in the production of haploid seed. Seed that has a haploid embryo, but normal triploid endosperm, advances to the second stage. That is, haploid seed and plants are any plant with a haploid embryo, independent of the ploidy level of the endosperm.

After selecting haploid seeds from the population, the selected seeds undergo chromosome doubling to produce doubled haploid seeds. A spontaneous chromosome doubling in a cell lineage will lead to normal gamete production or the production of unreduced gametes from haploid cell lineages. Application of a chemical compound, such as colchicine, can be used to increase the rate of diploidization. Colchicine binds to tubulin and prevents its polymerization into microtubules, thus arresting mitosis at metaphase, can be used to increase the rate of diploidization, i.e. doubling of the chromosome number. These chimeric plants are self-pollinated to produce diploid (doubled haploid) seed. This DH seed is cultivated and subsequently evaluated and used in hybrid testcross production. Descriptions of other breeding methods that are commonly used for different traits and crops can be found in one of several reference books (Allard, "Principles of Plant Breeding," John Wiley & Sons, NY, U. of CA, Davis, Calif., 50-98, 1960; Simmonds, "Principles of crop improvement," Longman, Inc., NY, 369-399, 1979; Sneep and Hendriksen, "Plant breeding perspectives," Wageningen (ed), Center for Agricultural Publishing and Documentation, 1979; Fehr, In: *Soybeans: Improvement, Production and Uses*, 2nd Edition, Monograph., 16:249, 1987; Fehr, "Principles of variety development," *Theory and Technique*, (Vol. 1) and *Crop Species Soybean* (Vol. 2), Iowa State Univ., Macmillan Pub. Co., NY, 360-376, 1987)

Methods of Genotyping with a Single Molecular Marker

Methods of genotyping with single molecular markers (e.g. soybean genomic polymorphism) can also be used to associate a phenotypic trait to a genotype in soybean plants. DNA or mRNA in tissue from at least two soybean plants having allelic DNA is assayed to identify the presence or absence of the polymorphisms provided as a molecular markers by the present invention. Associations between the molecular markers and the phenotypic traits are identified where the marker is identified in Table 1 or Table 3. In another aspect traits are associated to genotypes in a segregating population of soybean plants having allelic DNA in a specific locus of a chromosome which confers a phenotypic effect on a trait of interest and where the molecular marker is located either within or near this locus.

The methods of genotyping with single molecular markers (e.g. soybean genomic polymorphism) can also be used to select a parent plant, a progeny plant or a tester plant for breeding. In this case, the polymorphism is genetically linked to a chromosomal region that confers one or more desirable phenotypic trait(s). Selection of parent, progeny or tester soybean plants that contain the particular allelic state associated with the phenotypic trait(s) provides for accelerated and less costly breeding.

It is contemplated that certain soybean genomic polymorphisms disclosed herein in Table 1 or Table 3 can be directly linked to a given phenotypic trait in that they include certain allelic states that alter a regulatory or coding sequence of a gene that confers the trait or contributes to expression of the trait. Such traits include yield, lodging, maturity, plant height, fungal disease resistance, e.g. resistance to Asian Soybean rust (*Phakopsora pachyrhizi, Phakopsora meibomiae*), Soybean Anthracnose (*Colletotrichum truncatum, Colletotrichum dematium* var. *truncatum, Glomerella glycines*), *Phytophthora* Root and Stem Rot (*Phytophthora* sp.), White Mold (*Sclerotinia* sp.), *Sclerotinia* stem rot (*Sclerotinia sclerotiorum*), Sudden Death Syndrome (*Fusarium solani*), *Fusarium* root rot (*Fusarium* spp.), Charcoal rot (*Macrophomina phaseolina*), Brown Spot (*Septoria glycines*), *Pythium* seed decay (*Pythium aphanidermatum, Pythium debaryanum, Pythium irregulare, Pythium ultimum, Pythium myriotylum, Pythium torulosum*), Pod blight (*Diaporthe phaseolorum* var. *sojae*), Stem blight (*Phomopsis longicola*), *Phomopsis* seed decay (*Phomopsis* spp.), Downy Mildew (*Peronospora manshurica*), *Rhizoctonia* root and stem rot, *Rhizoctonia* aerial blight (*Rhizoctonia solani*), Brown Stem Rot (*Phialophora gregata*), Stem Canker (*Diaporthe phaseolorum* var. *caulivora*), Purple Seed Stain (*Cercospora kikuchii*), Target Spot (*Alternaria* sp.), Frogeye Leafspot (*Cercospora sojina*), Southern blight (*Sclerotium rolfsii*), Black leaf blight (*Arkoola nigra*), Black root rot (*Thielaviopsis basicola*), Choanephora leaf blight (*Choanephora infundibulifera, Choanephora trispora*), *Leptosphaerulina* leaf spot (*Leptosphaerulina trifolii*), *Mycoleptodiscus* root rot (*Mycoleptodiscus terrestris*), *Neocosmospora* stem rot (*Neocosmospora vasinfecta*), *Phyllosticta* leaf spot (*Phyllosticta sojicola*), *Pyrenochaeta* leaf spot (*Pyrenochaeta glycines*), Red crown rot (*Cylindrocladium crotalariae*), Red leaf blotch (*Dactuliochaeta glycines*), Scab (*Spaceloma glycines*), *Stemphylium* leaf blight (*Stemphylium botryosum*), Target spot (*Corynespora cassiicola*), *Nematospora coryli* (Yeast spot), and *Phymatotrichum omnivorum* (Cotton Root Rot), and other rots, blights, rusts, bacterial diseases, e.g., *Bacillus* seed decay (*Bacillus subtilis*), Bacterial blight (*Pseudomonas savastonoi* pv. *glycinea*), Bacterial crinkle-leaf (*Pseudomonas syringae* subsp. *syringae*), Bacterial pustule (*Xanthomonas axonopodis* pv. *glycines*), Bacterial tan spot (*Curtobacterium flaccumfaciens* pv. *flaccumfaciens*), Bacterial wilt (*Curtobacterium flaccumfaciens* pv. *flaccumfaciens, Ralstonia solanacearum*), and Wildfire (*Pseudomonas syringae* pv. *tabaci*), viral diseases, e.g., resistance to Alfafa mosaic virus, AMV (Alfamovirus), Bean pod mottle virus, BPMV (Comovirus), Bean yellow mosaic virus, BYMV (Potyvirus), Cowpea chlorotic mottle virus, CCMV (Bromovirus), Mung bean yellow mosaivc virus, MYMV (Begomovirus), Peanut mottle virus (Potyvirus), Peanut stripe virus, PStV (Potyvirus), Peanut stunt virus, PSV (Cucumovirus), Soybean chlorotic mottle virus, SbCMV (Caulimovirus), Soybean crinkle leaf virus, SCLV (Begomovirus), Soybean dwarf virus, SbDV (Luteovirus), Soybean mosaic virus, SMV (Potyvirus), Soybean severe stunt virus, SSSV (Nepovirus), and Tobacco ringspot virus, TRSV (Nepovirus), insect diseases, e.g., resistance to Soybean aphid (*Aphis glycines*), parasitic diseases, e.g. resistance to Soybean cyst nematode (*Heterodera glycines*), resistance to Root Knot Nematode (*Meloidogyne incognita, Meloidogyne arenaria*, and *Meloidogyne javanica*), Lance nematode (*Hoplolaimus Columbus, Hoplolaimus galeatus, Hoplolaimus magnistylus*), Lesion nematode (*Pratylenchus* spp.), Pin nematode (*Paratylenchus projectus, Paratylenchus tenuicaudatus*), Reniform nematode (*Rotylenchulus reniformis*), Ring nematode (*Criconemella ornata*), Sheath nematode (*Hemicycliophora* spp.), Spiral nematode (*Heliocotylenchus* spp.), Sting nematode (*Belonolainus gracilis, Belonolainus longicaudatus*), Stunt nematode (*Quinisulcius acutus, Tylenchorhynchus* spp.), and Stubby root nematode (*Paratrichodorus minor*), and the like, abiotic stress tolerance, e.g., drought tolerance, cold tolerance, heat tolerance, storm tolerance, nutrient deficiency, and the like, and quality traits, e.g., low linolenic acid content, enhanced starch content, enhanced oil content, decreased saturated fatty acid content, enhanced protein content, increased lysine content, and the like. When the soybean genomic polymorphism is directly linked to the trait in this manner, it is extremely useful in soybean breeding programs aimed at introducing that trait into many distinct soybean genetic backgrounds.

The use of molecular markers that are specifically associated with yield haplotypes is specifically contemplated herein. The soybean genomic DNA polymorphisms associated with yield haplotypes that can be used are from the group consisting of SEQ ID NO: 3122, 2914, 3984, 3608, 1448, 69, 1261, 3436, 1142, 80, 88, 980, 538, 1925, 3669, 2270, 1397, 3747, 888, 365, 2132, 1972, 459, 762, and SEQ ID NO: 1094. The soybean genomic DNA polymorphisms more closely associated with yield haplotypes are selected from the group consisting of SEQ ID NO: 3122, 2914, 3984, 3608, 1448, 69, 1261, 3436, 1142, and 80. Soybean genomic DNA polymorphisms with even greater degrees of association with yield haplotypes are selected from the group consisting of SEQ ID NO: 3122, 2914, 3984, 3608, and 1448. The soybean genomic polymorphisms that are most closely associated with a yield haplotype comprise the polymorphisms of SEQ ID NO: 3122.

Introgression of the genomic region associated with this single marker can be accelerated by using multiple markers to minimize linkage drag associated with genomic regions that may not confer agronomically elite properties. Introgression of the genomic region that is closely associated with this single marker can be accelerated by using multiple markers that immediately flank the single marker to minimize any linkage drag that is potentially associated with the closely associated genomic regions. Thus the use of a clustered set of 2, 5, 10 or 20 markers located with 10, 5, 2, or 1 cm of both the proximal and distal ends of a single marker can provide for introgression of the desired genomic region associated with the single marker while minimizing introgression of undesired immediate flanking regions. Introgression of the genomic region that is closely associated with this single marker can also be accelerated by using multiple markers that are distributed across the genome to minimize any linkage drag that is potentially associated with genomic regions located on distant regions of the same chromosome and on other chromosomes. This set of multiple markers may comprise 20 additional markers with at least one marker per chromosome. However, in preferred embodiments, the marker density is at least about 10 markers per chromosome, preferably about 20 markers per chromosome and more preferably at least about 100 markers per chromosome in order to efficiently discriminate between genomic regions from the donor and recipient parents. Use of multiple flanking markers that are either immediately linked to the single marker or are distributed across the genome can thus provide for maximum recovery of the recipient parent in selected progeny of a cross.

Methods of Genotyping with Sets of Soybean Genomic DNA Polymorphisms

Genotyping methods that employ sets of nucleic acid molecules that can type multiple distinct polymorphisms are specifically contemplated herein. In such methods, a finite number of at least two soybean genomic polymorphisms are typed. This finite number of soybean genomic polymorphisms queried can comprise at least 2, 5, 10 or 20 distinct polymorphisms that are represented as 2, 5, 10, or 20 distinct SEQ ID NO in Tables 1 or 3. Such methods of genotyping necessarily require the use of sets of nucleic acid molecules that can type sets of soybean genomic polymorphisms.

In certain applications, these methods of genotyping use a concentration of multiple molecular markers (i.e. soybean genomic polymorphisms) in a given chromosomal interval. High density fingerprints used to establish and trace the identity of germplasm can be obtained by performing the genotyping methods that use multiple molecular markers that are concentrated or clustered in certain chromosomal intervals and/or around certain genetic loci that confer certain traits. High density fingerprint information is useful for assessing germplasm diversity, performing genetic quality assurance functions, mining rare alleles, assessing exotic germplasm pools, and evaluating genetic purity. These high density finger prints can be used to establish a database of marker-trait associations to benefit an overall crop breeding program. High density fingerprints can also be used to establish and protect germplasm ownership. Sets of markers that are clustered around a desired chromosome interval or genetic trait can be selected from the mapped soybean polymorphisms provided in Table 3.

These methods of genotyping with multiple molecular markers can also be used to associate a phenotypic trait to a genotype in soybean plants. DNA or mRNA in tissue from at least two soybean plants having allelic DNA is assayed to identify the presence or absence of a set of finite series of polymorphisms provided as molecular markers by the present invention. Associations between the set of molecular markers and set of phenotypic traits are identified where the set of molecular markers comprises at least 2, at least 5, or at least 10, molecular markers linked to a polymorphic locus of the invention, e.g. at least 10 molecular markers linked to mapped polymorphisms, e.g. as identified in Table 3. In a more preferred aspect traits are associated to genotypes in a segregating population of soybean plants having allelic DNA in loci of a chromosome which confers a phenotypic effect on a trait of interest and where a molecular marker is located in such loci and where the degree of association among the molecular markers and between the polymorphisms and the traits permits determination of a linear order of the polymorphism and the trait loci. In such methods at least 5 molecular markers are linked to loci permitting disequilibrium mapping of the loci.

In still other applications, these methods of genotyping use molecular markers that are distributed across the genome of soybean. In these methods, the molecular marker can either be spread across a single chromosome, located on multiple chromosomes, located on all chromosomes or be located on each arm of each chromosome. In one specific embodiment, at least 1 of the molecular markers that is used in the genotyping method using a plurality of markers maps to each chromosome of all of the 20 soybean chromosomes, thus necessitating the typing of at least 20 soybean genomic DNA polymorphisms. However, other embodiments of this method where at least 10 soybean genomic DNA polymorphisms map to each chromosome, thus necessitating the typing of at least 200 soybean genomic DNA polymorphisms, are also contemplated. Similarly, still other embodiments that entail typing of at least 20 soybean genomic DNA polymorphisms on each chromosome (necessitating the typing of at least 400 polymorphisms) or typing of at least 50 soybean genomic DNA polymorphisms on each chromosome (necessitating the typing of at least 1,000 polymorphisms) are also contemplated. Embodiments that entail typing of at least 100 soybean genomic DNA polymorphisms on each chromosome (necessitating the typing of at least 2000 polymorphisms) are also contemplated. Sets of markers that are distributed across the genome of soybean can be selected from the mapped soybean polymorphisms provided in Table 3 for use in these methods.

Methods of genotyping that use molecular markers that are distributed across the genome of soybean can be used in a variety of applications. In one application, the methods of genotyping are used to select a parent plant, a progeny plant or a tester plant for breeding. A variety of applications of these genotyping methods to soybean breeding programs are contemplated. These genotyping methods can be used to facilitate introgression of one or more traits, genomic loci, and/or transgene insertions from one genetic background to a distinct genetic background. In general, the set of selected markers in progeny plants from out-crossed populations is queried to identify and select individual progeny that contain the desired traits, genomic loci, and/or transgene insertions yet comprises as many alleles from the distinct genetic background from the outcross as possible. Such methods can accelerate introgression of the desired traits, genomic loci, and/or transgene insertions into a new genetic background by several generations.

These methods also provide for screening of traits by interrogating a collection of molecular markers, such as SNPs, at an average density of less than about 10 cM on a genetic map of soybean. The presence or absence of a molecular marker linked to a polymorphic locus of Table 1 or Table 3 can be analyzed in the context of one or more phenotypic traits in order to identify one or more specific molecular marker alleles at one or more genomic regions that are associated with one or more of said traits. In another aspect of the invention the molecular markers are used to identify haplotypes which are allelic segments of genomic DNA characterized by at least two polymorphisms in linkage disequilibrium and wherein said polymorphisms are in a genomic windows of not more than 10 centimorgans in length, e.g. not more than about 8 centimorgans or smaller windows, e.g. in the range of say 1 to 5 centimorgans. In certain embodiments of these methods, set of such molecular markers to identify a plurality of haplotypes in a series of adjacent genomic windows in each soybean chromosome, e.g. providing essentially full genome coverage with such windows. With a sufficiently large and diverse breeding population of soybean, it is possible to identify a high quantity of haplotypes in each window, thus providing allelic DNA that can be associated with one or more traits to allow focused marker assisted breeding. Thus, an aspect of the soybean analysis of this invention further comprises the steps of characterizing one or more traits for said population of soybean plants and associating said traits with said allelic SNP or Indel polymorphisms, preferably organized to define haplotypes. Such traits include yield, lodging, maturity, plant height, fungal disease resistance, e.g. resistance to Asian Soybean rust (*Phakopsora pachyrhizi, Phakopsora meibomiae*), Soybean Anthracnose (*Colletotrichum truncatum, Colletotrichum dematium* var. *truncatum, Glomerella glycines*), Phytophthora Root and Stem Rot (*Phytophthora* sp.), White Mold (*Sclerotinia* sp.), *Sclerotinia* stem rot (*Sclerotinia sclerotiorum*), Sudden Death Syndrome (*Fusarium solani*), *Fusarium* root rot (*Fusarium* spp.), Charcoal rot (*Macrophomina phaseolina*), Brown Spot (*Septoria glycines*), Pythium seed decay (*Pythium aphanidermatum, Pythium debaryanum, Pythium irregulare, Pythium ultimum, Pythium myriotylum, Pythium torulosum*), Pod blight (*Diaporthe phaseolorum* var. *sojae*), Stem blight (*Phomopsis longicola*), *Phomopsis* seed decay (*Phomopsis* spp.), Downy Mildew (*Peronospora manshurica*), *Rhizoctonia* root and stem rot, *Rhizoctonia* aerial blight (*Rhizoctonia solani*), Brown Stem Rot (*Phialophora gregata*), Stem Canker (*Diaporthe phaseolorum* var. *caulivora*), Purple Seed Stain (*Cercospora kikuchii*), Target Spot (*Alternaria* sp.), Frogeye Leafspot (*Cercospora sojina*), Southern blight (*Sclerotium rolfsii*), Black leaf blight (*Arkoola nigra*), Black root rot (*Thielaviopsis basicola*), Choanephora leaf blight (*Choanephora infundibulifera, Choanephora trispora*), Leptosphaerulina leaf spot (*Leptosphaerulina trifolii*), Mycoleptodiscus root rot (*Mycoleptodiscus terrestris*), Neocosmospora stem rot (*Neocosmospora vasinfecta*), Phyllosticta leaf spot (*Phyllosticta sojicola*), Pyrenochaeta leaf spot (*Pyrenochaeta glycines*), Red crown rot (*Cylindrocladium crotalariae*), Red leaf blotch (*Dactuliochaeta glycines*), Scab (*Spaceloma glycines*), Stemphylium leaf blight (*Stemphylium botryosum*), Target spot (*Corynespora cassiicola*), *Nematospora coryli* (Yeast spot), and *Phymatotrichum omnivorum* (Cotton Root Rot), and other rots, blights, rusts, bacterial diseases, e.g., *Bacillus* seed decay (*Bacillus subtilis*), Bacterial blight (*Pseudomonas savastonoi* pv. *glycinea*), Bacterial crinkleleaf (*Pseudomonas syringae* subsp. *syringae*), Bacterial pustule (*Xanthomonas axonopodis* pv. *glycines*), Bacterial tan spot (*Curtobacterium flaccumfaciens* pv. *flaccumfaciens*), Bacterial wilt (*Curtobacterium flaccumfaciens* pv. *flaccumfaciens, Ralstonia solanacearum*), and Wildfire (*Pseudomonas syringae* pv. *tabaci*), viral diseases, e.g., resistance to Alfafa mosaic virus, AMV (Alfamovirus), Bean pod mottle virus, BPMV (Comovirus), Bean yellow mosaic virus, BYMV (Potyvirus), Cowpea chlorotic mottle virus, CCMV (Bromovirus), Mung bean yellow mosaivc virus, MYMV (Begomovirus), Peanut mottle virus (Potyvirus), Peanut stripe virus, PStV (Potyvirus), Peanut stunt virus, PSV (Cucumovirus), Soybean chlorotic mottle virus, SbCMV (Caulimovirus), Soybean crinkle leaf virus, SCLV (Begomovirus), Soybean dwarf virus, SbDV (Luteovirus), Soybean mosaic virus, SMV (Potyvirus), Soybean severe stunt virus, SSSV (Nepovirus), and Tobacco ringspot virus, TRSV (Nepovirus), insect diseases, e.g., resistance to Soybean aphid (*Aphis glycines*), parasitic diseases, e.g. resistance to Soybean cyst nematode (*Heterodera glycines*) or resistance to Root Knot Nematode (*Meloidogyne incognita, Meloidogyne arenaria,* and *Meloidogyne javanica*), Lance nematode (*Hoplolaimus Columbus, Hoplolaimus galeatus, Hoplolaimus magnistylus*), Lesion nematode (*Pratylenchus* spp.), Pin nematode (*Paratylenchus projectus, Paratylenchus tenuicaudatus*), Reniform nematode (*Rotylenchulus reniformis*), Ring nematode (*Criconemella ornata*), Sheath nematode (*Hemicycliophora* spp.), Spiral nematode (*Heliocotylenchus* spp.), Sting nematode (*Belonolainus gracilis, Belonolainus longicaudatus*), Stunt nematode (*Quinisulcius acutus, Tylenchorhynchus* spp.), and Stubby root nematode (*Paratrichodorus minor*), and the like, abiotic stress tolerance, e.g., drought tolerance, cold tolerance, heat tolerance, storm tolerance, nutrient deficiency, and the like, and quality traits, e.g., low linolenic acid content, enhanced starch content, enhanced oil content, decreased saturated fatty acid content, enhanced protein content, increased lysine content, and the like.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

This example illustrates the preparation of reduced representation libraries using enzymes which are sensitive to methylated cytosine residues in order to enrich for unique/ coding-sequence genomic DNA.

Genomic DNA extraction methods are well known in the art. A preferred method which maximizes both yield and convenience is to extract DNA using "PLANT DNAZOL REAGENT" from Life Technologies (Grand Island, N.Y.). Briefly, frozen leaf tissue is ground in liquid nitrogen in a mortar and pestle. The ground tissue is then extracted with DNAzo 1 reagent. This removes cellular proteins, cell wall material and other debris. Following extraction with this reagent, the DNA is precipitated, washed, resuspended, and treated with RNAse to remove RNA. The DNA is precipitated again, and resuspended in a suitable volume of TE (so that concentration is 1 µg/µl). The genomic DNA is ready to use in library construction.

Genomic DNA from two soybean lines which are to be compared for polymorphism detection are digested separately with Pst I restriction endonuclease which provides the ends of the DNA fragments with sticky ends which can ligate into a plasmid with the same restriction site. For instance, 100 units of Pst I is added to 20 μg of DNA and incubated at 37° C. for 8 hours. The digested DNA product is separated by electrophoresis on a 1% low-melting-temperature-agarose gel to separate the DNA fragments by size. The digested DNA from the two soybean lines is loaded side by side on the gel (with one lane in between as a spacer). Both a 1-KB DNA ladder marker and a 100-bp DNA ladder marker are loaded on each side of the two soybean DNA lanes. These markers act as a guide for size fractionation of the digested soybean DNA. Fragments in the range of 500 to 3000 bp are excised incrementally from the gel in size fractions of 500-600 bp, 600-700 bp, 700-800 bp, 800-900 bp, 900-1100 bp, 1100-1500 bp, 1500-2000 bp, 2000-2500 bp and 2500-3000 bp. DNA in each fraction is purified using β-agarase and ligated into the Pst I cloning site of pUC18. The plasmid ligation products are transformed by electroporation into DH10B E. coli bacterial hosts to produce reduced representation libraries. For instance, about 500 ng of the size-selected DNA is ligated to 50 ng dephosphorylated pUC18 vector.

Transformation is carried out by electroporation and the transformation efficiency for reduced representation Pst I libraries is approximately 50,000-300,000 transformants from one microliter of ligation product or 1000 to 6000 transformants/ng DNA.

Basic tests to evaluate the quality include the average insert size, chloroplast/mitochondrial DNA content, and the fraction of repetitive sequence.

The determination of the average insert size of the library is assessed during library construction. Every ligation is tested to determine the average insert size by assaying 10-20 clones per ligation. DNA is isolated from recombinant clones using a standard mini preparation protocol, digested with Pst I to free the insert from the vector and then sized using 1% agarose gel electrophoresis (Maule, *Molecular Biotechnology* 9:107-126 (1998), the entirety of which is herein incorporated by reference).

The chloroplast/mitochondrial DNA content, and the percentage of repetitive sequence in the library is estimated by sequencing a small sample of clones (400), and cross checking the sequence obtained against various sequence databases. Some repetitive elements are not present in the databases, but can nevertheless often be identified by the large number of copies of the same sequence. For instance, after sequencing a set of 400 clones any sequence that is not filtered by the repetitive element database, but yet is present more than 10 times in the sample is considered a repetitive element.

Soybean reduced representation libraries of the present invention are constructed by inserting coding region enriched DNA obtained from the following soybean lines: A2869, A3244, CX400, AG2403, AG2801, DKB31-51, AG3602, CMA5901C0C, A5427, N94-552, Hutchison, Essex, Accomac, Lee74, AG4201, AG5501, AG5605, AG4403, HS1, PIC, Minsoy, Noir, and Williams82.

Example 2

This example illustrates the determination of soybean genomic DNA sequence from clones in reduced representation libraries prepared in Example 1. Two basic methods can be used for DNA sequencing, the chain termination method of Sanger et al., *Proc. Natl. Acad. Sci. USA* 74:5463-5467 (1977) and the chemical degradation method of Maxam and Gilbert, *Proc. Natl. Acad. Sci. USA* 74:560-564 (1977). Automation and advances in technology such as the replacement of radioisotopes with fluorescence-based sequencing have reduced the effort required to sequence DNA (Craxton, Methods, 2:20-26 (1991), Ju et al., *Proc. Natl. Acad. Sci. USA* 92:4347-4351 (1995) and Tabor and Richardson, *Proc. Natl. Acad. Sci. USA* 92:6339-6343 (1995). Automated sequencers are available from, for example, Applied Biosystems, Foster City, Calif. (ABI PRISM® SYSTEMS); Pharmacia Biotech, Inc., Piscataway, N.J. (Pharmacia ALF), LI-COR, Inc., Lincoln, Nebr. (LI-COR 4,000) and Millipore, Bedford, Mass. (Millipore BaseStation).

Sequence base calling from trace files and quality scores are assigned by PHRED which is available from CodonCode Corporation, Dedham, Mass. and is described by Brent Ewing, et al. "Base-calling of automated sequencer traces using phred", 1998, Genome Research, Vol. 8, pages 175-185 and 186-194, incorporated herein by reference.

After the base calling is completed, sequence quality is improved by cutting poor quality end sequence. If the resulting sequence is less than 50 bp, it is deleted. Sequence with an overall quality of less than 12.5 is deleted. And, contaminating sequence, e.g. E. coli BAC and vector sequences and sub-cloning vector, are removed. Contigs are assembled using PANGEA CLUSTERING AND ALIGNMENT TOOLS which is available from DoubleTwist Inc., Oakland, Calif. by comparing pairs of sequences for overlapping bases. The overlap is determined using the following high stringency parameters: word size=8; window size=60; and identity is 93%. The clusters are reassembled using PHRAP fragment assembly program which is available from CodonCode Corporation using a "repeat stringency" parameter of 0.5 or lower. The final assembly output contains a collection of sequences including contig sequences which represent the consensus sequence of overlapping clustered sequences (contigs) and singleton sequences which are not present in any cluster of related sequences (singletons). Collectively, the contigs and singletons resulting from a DNA assembly are referred to as islands.

Example 3

This example illustrates identification of SNP and Indel polymorphisms by comparing alignments of the sequences of contigs and singletons from at least two separate soybean lines as prepared as in example 2. Sequence from multiple soybean lines is assembled into loci having one or more polymorphisms, i.e. SNPs and/or Indels. Candidate polymorphisms are qualified by the following parameters:

The minimum length of a contig or singleton for a consensus alignment is 200 bases.

The percentage identity of observed bases in a region of 15 bases on each side of a candidate SNP, is 75%.

The minimum BLAST quality in each contig at a polymorphism site is 35.

The minimum BLAST quality in a region of 15 bases on each side of the polymorphism site is 20.

A plurality of loci having qualified polymorphisms are identified as having consensus sequence as reported as SEQ ID NO: 1 through SEQ ID NO: 7800. The qualified SNP and Indel polymorphisms in each locus are identified in Table 1. More particularly, Table 1 identifies the type and location of the polymorphisms as follows:

SEQ_NUM refers to the SEQ ID NO. (sequence ID number) of the polymorphic soybean DNA locus.

CONSSEQ_ID refers to an arbitrary identifying name for the polymorphic soybean DNA locus.

MUTATION_ID refers to an arbitrary identifying name for each polymorphism.

START_POS refers to the position in the nucleotide sequence of the polymorphic soybean DNA locus where the polymorphism begins.

END_POS refers to the position in the nucleotide sequence of the polymorphic soybean DNA locus where the polymorphism ends; for SNPs the START_POS and END_POS are common.

TYPE refers to the identification of the polymorphism as an SNP or IND (Indel).

ALLELE and STRAIN refers to the nucleotide sequence of a polymorphism in a specific allelic soybean variety.

Example 4

This example illustrates the use of primer base extension for detecting a SNP polymorphism.

A small quantity of soybean genomic DNA (e.g. about 10 ng) is amplified using the forward and reverse PCR primers which are designed to have an annealing temperature of 55° C. to the template, i.e., around a polymorphism of a particular molecular marker. The PCR product is added to a new plate in which the extension primer is covalently bound to the surface of the reaction wells in a GBA plate. Extension mix containing DNA polymerase, the two differentially labeled ddNTPs, and extension buffer is added. The GBA plate is incubated at 42° C. for 15 min to allow extension. The reaction mix is removed from the wells by washing with a suitable buffer. The two labels are detected by sequential incubation with primary and secondary detection reagents for each of the labels. Incorporation of a specific ddNTP-FITC is measured by incubation with HRP-anti-FITC, followed by washing the wells, followed by incubation in a buffer containing a chromogenic substrate for HRP. The extent of the reaction is determined spectrophotometrically for each well at the wavelength appropriate for the product of the HRP reaction. The wells are washed again, and the procedure is repeated with AP-streptavidin, followed by a chromogenic substrate for AP, and spectrophotometry at the wavelength appropriate for the AP reaction product.

Analysis of Results.

The extent of incorporation of each labeled ddNTP is inferred from the absorbance measured for the reaction products of the detection steps specific label, and the genotype of the sample is inferred from the ratios of these absorbances as compared to a standard of known genotype and a no-template control reactions. In the most common practice, the absorbances observed for each data point are plotted against each other in a scatter plot, producing an "allelogram". A successful genotyping assay using the single base extension assay of this example provides an allelogram as illustrated in FIG. 2 where the data points are grouped into four clusters: Homozygote 1 (e.g., the A allele), homozygote 2 (e.g., the G allele), heterozygotes (each sample containing both alleles), and a "no signal" cluster resulting from no-template controls, or failed amplification or detection.

Example 5

This example illustrates the use of a labeled probe degradation assay for detecting a SNP polymorphism. A quantity of soybean genomic template DNA (e.g. about 2-20 ng) is mixed in 5 ul total volume with four oligonucleotides, as described in Table 2, i.e. forward primer, reverse primer, hybridization probe having a VIC reporter attached to the 5' end and hybridization probe having a FAM reporter attached to the 5' end as well as PCR reaction buffer containing the passive reference dye ROX. The PCR reaction is conducted for 35 cycles using a 60° C. annealing-extension temperature. Following the reaction, the fluorescence of each fluorophore as well as that of the passive reference is determined in a fluorimeter. The fluorescence value for each fluorophore is normalized to the fluorescence value of the passive reference. The normalized values are plotted against each other for each sample to produce an allelogram. A successful genotyping assay using the primers and hybridization probes of this example provides an allelogram with data points in clearly separable clusters as illustrated in FIG. 2.

Table 2. Examples of molecular marker assays using labeled probe degradation detection of SNP polymorphisms. Each assay provides two oligonucleotides primers, to amplify the region spanning the polymorphism, and two oligonucleotides probes, which have fluorogenic reporter molecules attached for SNP allele detection. Useful reporter dyes include, but are not limited to, 6-carboxy-4,7,2',7'-tetrachlorofluorecein (TET), 2'-chloro-7'-phenyl-1,4-dichloro-6-carboxyfluorescein (VIC) and 6-carboxyfluorescein phosphoramidite (FAM). A useful quencher is 6-carboxy-N,N,N',N'-tetramethylrhodamine (TAMRA).

| Marker SEQ ID | CONSSEQ_ ID | PRIMER SEQ ID NO | Sequence type | Sequence | Allele |
|---|---|---|---|---|---|
| 654 | 20052164-CON.1 | SEQ ID NO: 7801 | Forward Primer | CGTTCTCGACTTCAACCATATGTG | A |
| 654 | 20052164-CON.1 | SEQ ID NO: 7802 | Probe 1 | CCATGGTATCATAGGCA | T |
| 654 | 20052164-CON.1 | SEQ ID NO: 7803 | Probe 2 | CCATGGTATCGTAGGCA | C |
| 654 | 20052164-CON.1 | SEQ ID NO: 7804 | Reverse Primer | GCATGGAATAAAGCGGAAAGGAA AG | |
| 650 | 20052160-CON.1 | SEQ ID NO: 7805 | Forward Primer | TTTAACTCACTACTTGAGCTTGAT TTCATCT | |
| 650 | 20052160-CON.1 | SEQ ID NO: 7806 | Probe 1 | CTATGCCTAAGTATTCTT | G |
| 650 | 20052160-CON.1 | SEQ ID NO: 7807 | Probe 2 | CTATGCCTAAATATTCTT | A |
| 650 | 20052160-CON.1 | SEQ ID NO: 7808 | Reverse Primer | CAACAAACTTAGATTAACAACAC CAATTAGGT | |

To confirm that an assay produces accurate results, each new assay is performed on a number of replicates of samples of known genotypic identity representing each of the three possible genotypes, i.e. two homozygous alleles and a heterozygous sample. To be a valid and useful assay, it must produce clearly separable clusters of data points, such that one of the three genotypes can be assigned for at least 90% of the data points, and the assignment is observed to be correct for at least 98% of the data points. Subsequent to this validation step, the assay is applied to progeny of a cross between two highly inbred individuals to obtain segregation data, which are then used to calculate a genetic map position for the polymorphic locus.

Example 6

This example illustrates the genetic mapping of molecular markers in loci of this invention based on the genotypes of over 2000 SNPs for 476 $F_2$ plants originating from the cross of soy lines A3244 and AG5501. Before mapping, any loci showing distorted segregation (P<1e-5 for a Chi-square test of a 1:1 segregation ratio) are removed. A low alpha-level is used to account for the multiple-testing problem.

In one aspect, a map can be constructed using the JOINMAP version 2.0 software which is described by Stam, P. "Construction of integrated genetic linkage maps by means of a new computer package: JOINMAP, The Plant Journal, 3: 739-744 (1993); Stain, P. and van Ooijen, J. W. "JOINMAP version 2.0: Software for the calculation of genetic linkage maps (1995) CPRO-DLO, Wageningen. JOINMAP implements a weighted-least squares approach to multipoint mapping in which information from all pairs of linked loci (adjacent or not) is incorporated. Linkage groups are formed using a LOD threshold of 5.0. The SSR and RFLP public markers are used to assign linkage groups to chromosomes. Linkage groups are merged within chromosomes before map construction.

Other approaches to mapping high density markers are known in the art; see, for example, Winkler et al. (Genetics 164:741-745 (2003)), for the utility of IRIs for higher resolution mapping. See also, Jansen et al. (Theor Appl Genet 102:1113-1122 (2001)). In many conditions, the approach of Jansen et al. yields a close approximation to a maximum-likelihood map. Further, a map estimated by this approach agrees quite closely with the map obtained using JOINMAP 2.0. In addition, combinations of methods described above and incorporated herein by reference may be used to best leverage marker data under a range of population structure as well as computational constraints.

In another aspect of the present invention, Kosambi's mapping function is used to convert recombination fractions to map distances. Mapped SNP molecular markers are identified in Table 3 where "LG" identifies the linkage group or chromosome and "Position" identifies the distance measured in cM from the 5' end of a soybean chromosome for the SNP identified by "Consseq_ID". For certain of the mapped polymorphic markers listed in Table 3, the Mutation ID is listed more than once which indicates that the mapping was conducted based on multiple genotyping assays. The map locations for multiple genotyping assays generally serve to confirm map location except in the case where map locations are divergent, e.g. due to error in the design or practice of an assay. The density and distribution of the mapped molecular markers is shown in FIG. 1.

Example 7

This example illustrates methods of the invention using molecular markers disclosed in Table 1 and in the DNA sequences of SEQ ID NO:1-7800.

A breeding population of soybean with diverse heritage is analyzed using primer pairs and probe pairs prepared as indicated in Example 5 for each of the molecular markers identified in Table 1 based on sequences of SEQ ID NO:1-7800. Closely linked molecular markers are identified as characterizing haplotypes within adjacent genomic windows of about 10 centimorgans across the soybean genome. Haplotypes representing at least 4% of the population are associated with trait values identified for each member of the soybean population including the trait values for yield, maturity, lodging, plant height, rust resistance, drought tolerance and cold germination. The trait values for each haplotype are ranked in each 10 centimorgan window. Progeny seed from randomly-mated members of the population are analyzed for the identity of haplotypes in each window. Progeny seed are selected for planting based on high trait values for haplotypes identified in said seeds.

Example 8

This example illustrates the identification of polymorphisms that are useful for obtaining a parent plant, a progeny plant or a tester plant for breeding with a preferred trait. In this particular example, polymorphisms have been selected for usefulness in identifying plants with a preferred yield trait for illustrative purposes. However, it is also anticipated that other markers useful for identifying other preferred traits can be identified in a similar manner (i.e. by noting the location of a polymorphism's genetic map position within a haplotype window). It is further anticipated that the specific markers disclosed in this Example may also find other uses in addition to serving as markers for yield traits.

First, haplotype windows associated with yield were identified as disclosed in U.S. Patent Application Ser. No. 60/837, 864. The map positions disclosed in Table 3 were used to identify markers of the present invention that are located in the haplotype window(s) comprising the preferred haplotypes for yield and that can be used as markers for these regions. 25 polymorphisms coinciding with 25 haplotype windows that comprise the 25 haplotypes in Monsanto soybean germplasm associated with a yield advantage were selected. Two (2) markers are thus provided for most of these yield haplotype windows. The specific markers that can be used to identify plants for breeding with the preferred yield trait can be selected from the group consisting of SEQ ID NO: 3122, 2914, 3984, 3608, 1448, 69, 1261, 3436, 1142, 80, 88, 980, 538, 1925, 3669, 2270, 1397, 3747, 888, 365, 2132, 1972, 459, 762, and SEQ ID NO: 1094.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

Various patent and non-patent publications are cited herein, the disclosures of each of which are incorporated herein by reference in their entireties.

As various modifications could be made in the constructions and methods herein described and illustrated without departing from the scope of the invention, it is intended that all matter contained in the foregoing description or shown in the accompanying drawings shall be interpreted as illustrative rather than limiting. The breadth and scope of the present invention should not be limited by any of the above-described exemplary embodiments, but should be defined only in accordance with the following claims appended hereto and their equivalents.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09271455B2). An electronic copy of the "Sequence Listing" will also be available from the USPTO upon request and payment of the fee set forth in 37 CFR 1.19(b)(3).

What is claimed is:

1. A method of genotyping a soybean plant to select a parent plant, a progeny plant or a tester plant with increased yield for breeding, said method comprising the steps of:
   a. obtaining a DNA or RNA sample from a tissue of at least one soybean plant;
   b. determining the allelic state of the soybean genomic DNA polymorphism of SEQ ID NO: 3122 associated with increased yield, for said sample from step (a); and
   c. using said determination of the allelic state of the soybean genomic DNA polymorphism of SEQ ID NO: 3122 of step (b) to select a parent plant, a progeny plant or a tester plant with increased yield for breeding.

2. The method according to claim 1, wherein the soybean genomic DNA polymorphism of SEQ ID NO: 3122 is a first polymorphism used to identify plants for breeding with increased yield and wherein the allelic state of one or more additional soybean genomic polymorphisms selected from the group consisting of SEQ ID NO: 2914, 3984, 3608, 1448, 69, 1261, 3436, 1142, 80, 88, 980, 538, 1925, 3669, 2270, 1397, 3747, 888, 365, 2132, 1972, 459, 762, and SEQ ID NO: 1094, associated with increased yield, is also determined to select a parent plant, a progeny plant, or a tester plant with increased yield for breeding.

3. The method according to claim 2, wherein the allelic state of at least seven or more soybean genomic polymorphisms selected from the group consisting of SEQ ID NO: 2914, 3984, 3608, 1448, 69, 1261, 3436, 1142, 80, 88, 980, 538, 1925, 3669, 2270, 1397, 3747, 888, 365, 2132, 1972, 459, 762, and SEQ ID NO: 1094, associated with increased yield, is also determined to select a parent plant, a progeny plant, or a tester plant with increased yield for breeding.

4. A method of genotyping a soybean plant to select a parent plant, a progeny plant or a tester plant with increased yield for breeding, said method comprising the steps of:
   a. obtaining a DNA or RNA sample from a tissue of at least one soybean plant;
   b. determining the allelic state of a set of soybean genomic DNA polymorphisms comprising the soybean genomic DNA polymorphism of SEQ ID NO: 3122 associated with increased yield, and one or more additional polymorphisms selected from the group consisting of SEQ ID NO: 2914, 3984, 3608, 1448, 69, 1261, 3436, 1142, 80, 88, 980, 538, 1925, 3669, 2270, 1397, 3747, 888, 365, 2132, 1972, 459, 762, and 1094, associated with increased yield, for said sample from step (a), wherein said allelic state is determined with a set of nucleic acid molecules that provide for typing of said soybean genomic DNA polymorphisms; and
   c. using said determination of the allelic state of the set of soybean genomic DNA polymorphisms comprising the soybean genomic DNA polymorphism of SEQ ID NO: 3122 associated with increased yield, and one or more additional polymorphisms selected from the group consisting of SEQ ID NO: 2914, 3984, 3608, 1448, 69, 1261, 3436, 1142, 80, 88, 980, 538, 1925, 3669, 2270, 1397, 3747, 888, 365, 2132, 1972, 459, 762, and 1094, associated with increased yield, to select a parent plant, a progeny plant or a tester plant with increased yield for breeding.

5. The method of genotyping a soybean plant of claim 4, wherein said set of soybean genomic DNA polymorphisms comprises the soybean genomic DNA polymorphism of SEQ ID NO: 3122 associated with increased yield, and at least four or more additional polymorphisms selected from the group consisting of SEQ ID NO: 2914, 3984, 3608, 1448, 69, 1261, 3436, 1142, 80, 88, 980, 538, 1925, 3669, 2270, 1397, 3747, 888, 365, 2132, 1972, 459, 762, and 1094, associated with increased yield.

6. The method of genotyping a soybean plant of claim 4, wherein said set of soybean genomic DNA polymorphisms comprises the soybean genomic DNA polymorphism of SEQ ID NO: 3122 associated with increased yield, and at least one or more additional polymorphisms selected from the group consisting of SEQ ID NO: 2914, 3984, 3608, 1448, 69, 1261, 3436, 1142, and 80, associated with increased yield.

* * * * *